US011437582B2

(12) United States Patent
Duan et al.

(10) Patent No.: US 11,437,582 B2
(45) Date of Patent: Sep. 6, 2022

(54) ORGANIC ELECTROLUMINESCENT DEVICE AND MANUFACTURING METHOD THEREOF

(71) Applicants: KUNSHAN GO-VISIONOX OPTO-ELECTRONICS CO., LTD., Suzhou (CN); TSINGHUA UNIVERSITY, Beijing (CN)

(72) Inventors: Lian Duan, Beijing (CN); Dongdong Zhang, Beijing (CN); Song Liu, Beijing (CN); Jing Xie, Hebei (CN); Fei Zhao, Beijing (CN)

(73) Assignees: KUNSHAN GO-VISIONOX OPTO-ELECTRONICS CO., LTD., Kunshan (CN); TSINGHUA UNIVERSITY, Beijing (CN)

( * ) Notice: Subject to any disclaimer, the term of this patent is extended or adjusted under 35 U.S.C. 154(b) by 602 days.

(21) Appl. No.: 15/737,179

(22) PCT Filed: Jun. 15, 2016

(86) PCT No.: PCT/CN2016/085802
§ 371 (c)(1),
(2) Date: Dec. 15, 2017

(87) PCT Pub. No.: WO2016/202251
PCT Pub. Date: Dec. 22, 2016

(65) Prior Publication Data
US 2018/0175294 A1 Jun. 21, 2018

(30) Foreign Application Priority Data
Jun. 16, 2015 (CN) .......................... 201510334281.9

(51) Int. Cl.
*H01L 51/54* (2006.01)
*H01L 51/00* (2006.01)
(Continued)

(52) U.S. Cl.
CPC .......... *H01L 51/006* (2013.01); *C07C 211/61* (2013.01); *C07C 255/58* (2013.01);
(Continued)

(58) Field of Classification Search
CPC . H01L 51/001; H01L 51/0008; H01L 51/005; H01L 51/0081; H01L 51/5028; H01L 51/5048; H01L 51/56; H01L 51/0052; H01L 51/0056; H01L 51/5016; H01L 51/5024; H01L 51/5056; H01L 51/5072; H01L 51/006; H01L 51/0059; H01L 51/0061; H01L 51/0067; H01L 51/0068; H01L 51/0069; H01L 51/007; H01L 51/0071; H01L 51/0072; H01L 51/0077; H01L 51/0092; H01L 51/5012; H01L 2251/5384; H01L 2251/5376; H01L 2251/558; C07C 211/61; C07C 255/58; C07C 317/36; C07C 2603/24; C07C 2603/97; C07D 209/80; C07D 209/86;
(Continued)

(56) References Cited

U.S. PATENT DOCUMENTS

2006/0063027 A1* 3/2006 Vestweber .......... H01L 51/0039
428/690
2006/0099447 A1* 5/2006 Lee ........................ C09K 11/06
428/690
(Continued)

FOREIGN PATENT DOCUMENTS

CN 101993440 A 3/2011
CN 101993440 A 3/2011
(Continued)

OTHER PUBLICATIONS

Zhang et al. Organic Electronics 2013, 14, 260-266. (Year: 2013).*
Decision of Rejection of Korea Application No. 10-2018-7000314.
KR KIPO, First Office Action, dated Dec. 20, 2018.
Bing et al., Progress in Next-Generation Organic Electroluminescent Materials: Material Design Beyond Exciton Statistics, Science China Press, vol. 43, No. 11, 2013, pp. 1457-1467. (English Abstract Attached).
International Search Report and Written opinion received in International Application No. PCT/CN2016/085802, dated Sep. 19, 2016, 18 pages including 9 pages of English Translation.
Park et al., Exciplex-Forming Co-Host for Organic Light-Emitting Diodes with Ultimate Efficiency, Materials Views, Adv. Funct. Mater., 2013, pp. 1-7.
(Continued)

*Primary Examiner* — Andrew K Bohaty
(74) *Attorney, Agent, or Firm* — Kilpatrick Townsend & Stockton

(57) ABSTRACT

Disclosed is an organic electroluminescent device, comprising a substrate and light emitting units formed in sequence on the substrate, characterized in that, each of the light emitting units comprises a first electrode layer (1), a light emitting layer (2) and a second electrode layer (3), the light emitting layer comprises a host material and a dye, the host material is made of materials having both electron transport capability and hole transport capability; at least one material in the host material has a CT excited triplet state energy level $T_1$ greater than its n-π excited triplet state energy level $S_1$, and $T_1$-$S_1 \leq 0.3$ eV; or, at least one material in the host material has a CT excited triplet state energy level $T_1$ greater than its n-π excited triplet state energy level $S_1$, and $T_1$-$S_1 \geq 1$ eV, with the difference between its n-π excited second triplet state energy level and its CT excited first singlet state energy level being in the range of −0.1 eV to 0.1 eV. The organic electroluminescent device configuration can sufficiently utilize the triplet state energy in the host material and the dye to increase the luminous efficiency and prolong the service life of the device.

7 Claims, 1 Drawing Sheet

(51) Int. Cl.

| | | |
|---|---|---|
| H01L 51/50 | (2006.01) | |
| C07C 211/61 | (2006.01) | |
| C07C 255/58 | (2006.01) | |
| C07C 317/36 | (2006.01) | |
| C07D 209/80 | (2006.01) | |
| C07D 209/86 | (2006.01) | |
| C07D 219/02 | (2006.01) | |
| C07D 221/20 | (2006.01) | |
| C07D 241/48 | (2006.01) | |
| C07D 265/38 | (2006.01) | |
| C07D 285/14 | (2006.01) | |
| C07D 403/10 | (2006.01) | |
| C07D 403/14 | (2006.01) | |
| C07D 413/10 | (2006.01) | |
| C07D 413/14 | (2006.01) | |
| C07D 417/04 | (2006.01) | |
| C07D 417/10 | (2006.01) | |
| C07D 417/14 | (2006.01) | |
| C07D 471/20 | (2006.01) | |
| C07D 487/14 | (2006.01) | |
| C07D 487/16 | (2006.01) | |
| C07F 1/02 | (2006.01) | |
| C07F 3/02 | (2006.01) | |
| C07F 3/06 | (2006.01) | |

(52) U.S. Cl.
CPC .......... *C07C 317/36* (2013.01); *C07D 209/80* (2013.01); *C07D 209/86* (2013.01); *C07D 219/02* (2013.01); *C07D 221/20* (2013.01); *C07D 241/48* (2013.01); *C07D 265/38* (2013.01); *C07D 285/14* (2013.01); *C07D 403/10* (2013.01); *C07D 403/14* (2013.01); *C07D 413/10* (2013.01); *C07D 413/14* (2013.01); *C07D 417/04* (2013.01); *C07D 417/10* (2013.01); *C07D 417/14* (2013.01); *C07D 471/20* (2013.01); *C07D 487/14* (2013.01); *C07D 487/16* (2013.01); *C07F 1/02* (2013.01); *C07F 3/02* (2013.01); *C07F 3/06* (2013.01); *H01L 51/007* (2013.01); *H01L 51/0059* (2013.01); *H01L 51/0061* (2013.01); *H01L 51/0067* (2013.01); *H01L 51/0068* (2013.01); *H01L 51/0069* (2013.01); *H01L 51/0071* (2013.01); *H01L 51/0072* (2013.01); *H01L 51/0077* (2013.01); *H01L 51/0092* (2013.01); *H01L 51/5012* (2013.01); *C07C 2603/24* (2017.05); *C07C 2603/97* (2017.05); *H01L 51/0008* (2013.01); *H01L 51/0052* (2013.01); *H01L 51/0056* (2013.01); *H01L 51/5016* (2013.01); *H01L 51/5024* (2013.01); *H01L 51/5056* (2013.01); *H01L 51/5072* (2013.01); *H01L 2251/5376* (2013.01); *H01L 2251/5384* (2013.01); *H01L 2251/558* (2013.01)

(58) Field of Classification Search
CPC .. C07D 219/02; C07D 221/20; C07D 241/48; C07D 265/38; C07D 285/14; C07D 403/10; C07D 403/14; C07D 413/10; C07D 413/14; C07D 417/04; C07D 417/10; C07D 417/14; C07D 471/20; C07D 487/14; C07D 487/16; C07F 1/02; C07F 3/02; C07F 3/06
See application file for complete search history.

(56) References Cited

U.S. PATENT DOCUMENTS

| | | | |
|---|---|---|---|
| 2010/0187977 A1* | 7/2010 | Kai | H01L 51/0072 313/504 |
| 2011/0062862 A1 | 3/2011 | Yamamoto et al. | |
| 2011/0279020 A1* | 11/2011 | Inoue | H01L 51/5024 313/504 |
| 2012/0001158 A1* | 1/2012 | Asari | H01L 51/0067 257/40 |
| 2012/0001537 A1* | 1/2012 | Lin | C09K 11/06 546/18 |
| 2012/0007070 A1* | 1/2012 | Kai | H05B 33/22 257/40 |
| 2012/0248968 A1 | 10/2012 | Ogiwara et al. | |
| 2012/0298975 A1 | 11/2012 | Iwakuma et al. | |
| 2013/0140549 A1* | 6/2013 | Xia | H01L 51/0072 257/40 |
| 2014/0001449 A1 | 1/2014 | Maunoury et al. | |
| 2015/0041784 A1* | 2/2015 | Shizu | C07D 251/24 257/40 |
| 2015/0060801 A1* | 3/2015 | Nishimura | C07D 403/14 257/40 |
| 2015/0155511 A1 | 6/2015 | Ohsawa et al. | |
| 2015/0174831 A1 | 6/2015 | Yolanda et al. | |
| 2015/0214489 A1* | 7/2015 | Parham | H01L 51/0067 252/301.16 |
| 2016/0056393 A1* | 2/2016 | Oikawa | H01L 51/0064 257/40 |
| 2016/0190478 A1 | 6/2016 | Nakanotani et al. | |
| 2017/0149007 A1 | 5/2017 | Ogiwara et al. | |

FOREIGN PATENT DOCUMENTS

| | | | | |
|---|---|---|---|---|
| CN | 103443949 A | 12/2013 | | |
| CN | 103443949 A | 12/2013 | | |
| CN | 104716268 A | 6/2015 | | |
| CN | 104716268 A | 6/2015 | | |
| EP | 2980876 A1 | 2/2016 | | |
| JP | 2015-038941 A | 2/2015 | | |
| JP | 2015038941 A | 2/2015 | | |
| JP | 2015065152 A | 4/2015 | | |
| JP | 2015078178 A | 4/2015 | | |
| KR | 10-2014-0015385 A | 2/2014 | | |
| KR | 1020140015385 A | 2/2014 | | |
| KR | 10-2014-0092710 A | 7/2014 | | |
| KR | 1020140092710 A | 7/2014 | | |
| KR | 1020150002534 A | 1/2015 | | |
| TW | 201510175 A | 3/2015 | | |
| TW | 201526337 A | 7/2015 | | |
| WO | WO-2004058911 A2 * | 7/2004 | .......... | C07D 209/86 |
| WO | 2012133188 A1 | 10/2012 | | |
| WO | WO-2013147205 A1 * | 10/2013 | ............. | H05B 33/10 |
| WO | WO-2013172255 A1 * | 11/2013 | .......... | C07D 413/04 |
| WO | 2014001593 A1 | 1/2014 | | |
| WO | WO-2014015931 A1 * | 1/2014 | .......... | C07D 405/14 |
| WO | 2014157610 A1 | 10/2014 | | |
| WO | 2015020217 A1 | 2/2015 | | |

OTHER PUBLICATIONS

First Office Action received in Chinese Application No. 201510334281.9, dated Jul. 27, 2017, 12 pages including 6 pages of English Translation.
Second Office Action received in Chinese Application No. 201510334281.9, dated Mar. 9, 2018, 25 pages including references.
First Office Action received in Taiwan Application No. 105118809, dated Dec. 16, 2016, 10 pages.
Decision of Rejection received in Taiwan Application No. 105118809, dated Apr. 18, 2018, 8 pages.
First Office Action of Japan application No. 2017-564638, dated Jan. 15, 2019.
European Search Report of application No. 16810992.4.
Dongdong Zhang et al: "High-Efficiency Fluorescent Organic Light-Emitting Devices Using Sensitizing Hosts with a Small Singlet-

(56) References Cited

OTHER PUBLICATIONS

Triplet Exchange Energy", Advanced Materials, vol. 26, No. 29, Aug. 1, 2014.
Hajime Nakanotani et al: "High-Efficiency organic light-emitting diodes with fluorescent emitters", Nature Communications, vol. 5, May 30, 2014.
Notification of Second Office Action for European corresponding Application No. 168109924.

* cited by examiner

ORGANIC ELECTROLUMINESCENT DEVICE AND MANUFACTURING METHOD THEREOF

CROSS REFERENCE TO RELATED APPLICATIONS

This application is a national phase filing under 35 U.S.C. § 371 of International Application No. PCT/CN2016/085802 filed Jun. 15, 2016, which claims priority from Chinese application number 201510334281.9, filed Jun. 16, 2015, the entire contents of which is hereby incorporated by reference herein.

TECHNICAL FIELD

The present invention relates to the technical field of organic electroluminescent devices, and in particular relates to an organic electroluminescent device with a single-layered organic layer.

BACKGROUND

An organic electroluminescent device (OLED) usually includes a plurality of pixels, and each pixel is composed of several sub-pixels. Currently, one widely used solution in small and medium sized devices is forming a pixel with three sub-pixels of red, green and blue. Each kind of sub-pixel comprises a hole transport layer, a light emitting layer, an electron transport layer, and a hole/exciton blocking layer arranged between the light emitting layer and the electron transport layer, wherein the light emitting layer comprises a blue light emitting layer, a green light emitting layer or a red light emitting layer. Besides, a green optical compensation layer and a red light emitting layer might be required to be arranged between the hole transport layer and an electrode layer, which further adds to the processing steps.

In order to solve the above-mentioned problem, it is explored to use a device configuration with a single-layered light emitting layer. However, in conventional OLED devices with single-layered light emitting layer, because most organic materials have imbalanced carrier injection and different carriers have hugely different transporting speed, the light emitting area easily shifts to the side of the injection electrode with a lower migration rate. In the condition of a metal electrode, this may easily cause light-emitting to be quenched by the electrode, which negatively affects the efficiency and service life of the device.

SUMMARY OF THE INVENTION

Thus, the present invention is intended to solve the technical problem that the organic electroluminescent devices in prior arts with the existing configuration of single-layered structure have a short service life because of exciton quenching, by providing an organic electroluminescent device that can sufficiently utilize the triplet state energy in the host material and the dye to increase the luminous efficiency and prolong the service life of the device.

The present invention also provides a preparation method of the above-mentioned organic electroluminescent device.

In order to solve the above-mentioned technical problem, the present invention adopts the following technical scheme:

An organic electroluminescent device comprises a substrate and light emitting units formed in sequence on the substrate, and each of the light emitting units comprises a first electrode layer, a light emitting layer and a second electrode layer, the light emitting layer comprises a host material and a dye, the host material is made of materials having both electron transport capability and hole transport capability; at least one material in the host material has a CT excited triplet state energy level $T_1$ greater than its n-π excited triplet state energy level $S_1$, and $T_1$-$S_1$≤0.3 eV; or, at least one material in the host material has a CT excited triplet state energy level $T_1$ greater than its n-π excited triplet state energy level $S_1$, and $T_1$-$S_1$≥1 eV, with the difference between its n-π excited second triplet state energy level and its CT excited first singlet state energy level being in the range of −0.1 eV to 0.1 eV.

Preferably, the host material is an exciplex, and the exciplex is a thermal activating delayed fluorescence material.

Alternatively, the host material is an exciplex made from an electron transport type material and a hole transport type material at a mass ratio of 1:9 to 9:1. Wherein, the electron transport type material and/or the hole transport type material has $T_1$-$S_1$≤0.3 eV; or, the electron transport type material and/or the hole transport type material has $T_1$-$S_1$≥1 eV, with the difference between the n-π excited second triplet state energy level and the CT excited first singlet state energy level of the host material being in the range of −0.1 eV to 0.1 eV.

Alternatively, the host material is composed of a thermal activating delayed fluorescence material and a hole transport type material at a mass ratio of 1:9 to 9:1. Wherein, the thermal activating delayed fluorescence material and/or the hole transport type material has $T_1$-$S_1$≤0.3 eV; or, the thermal activating delayed fluorescence material and/or the hole transport type material has $T_1$-$S_1$≥1 eV, with the difference between the n-π excited second triplet state energy level and the CT excited first singlet state energy level of the host material being in the range of −0.1 eV to 0.1 eV.

Alternatively, the host material is composed of a thermal activating delayed fluorescence material and an electron transport type material at a mass ratio of 1:9 to 9:1. Wherein, the thermal activating delayed fluorescence material and/or the electron transport type material has $T_1$-$S_1$≤0.3 eV; or, the thermal activating delayed fluorescence material and/or the electron transport type material has $T_1$-$S_1$≥1 eV, with the difference between the n-π excited second triplet state energy level and the CT excited first singlet state energy level of the host material being in the range of −0.1 eV to 0.1 eV.

The dye is made of a fluorescence material and/or a phosphorescence material, the fluorescence material has a doping concentration of 0.5-10 wt %, the phosphorescence material has a doping concentration of 0.5-20 wt %.

The light emitting layer has a thickness of 50 nm-150 nm.

The electron transport type material is tri-(8-oxyquinoline)-aluminum, 2,9-dimethyl-4,7-diphenyl-1,10-o-phenanthroline, 4,7-diphenyl-1,10-o-phenanthroline, di-(2-methyl-8-quinolyl)-4-phenyl-phenoxide-aluminum(III), 1,3,5-tri-(1-phenyl-1H-benzimidazole-2-yl)-benzene, or 1,3,5-tri-[(3-pyridyl)-3-phenyl]-benzene.

The hole transport type material is N,N'-di-(1-naphthyl)-N,N'-diphenyl-1,1'-biphenyl-4,4'-diamine, N,N'-diphenyl-N,N'-di-(m-methyl-phenyl)-1,1'-biphenyl-4,4'-diamine, 4,4'-cyclohexyl-di-[N,N-di-(4-methyl-phenyl)]-phenylamine, 4,4'-N,N'-di-carbazole-biphenyl, 4,4',4''-tri-(carbazole-9-yl)-triphenylamine, or 1,3-di-(carbazole-9-yl)-benzene.

The thermal activating delayed fluorescence (TADF) material has a structure selected from the following structural formulas (1-1) to (1-100):
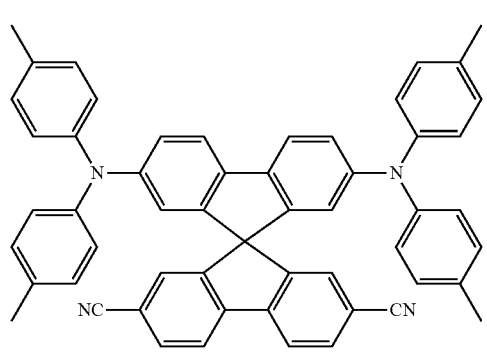
1-1
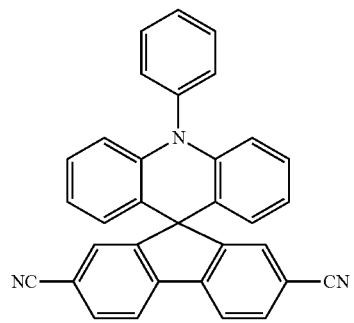
1-2
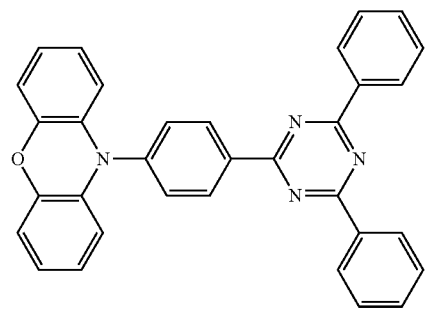
1-3
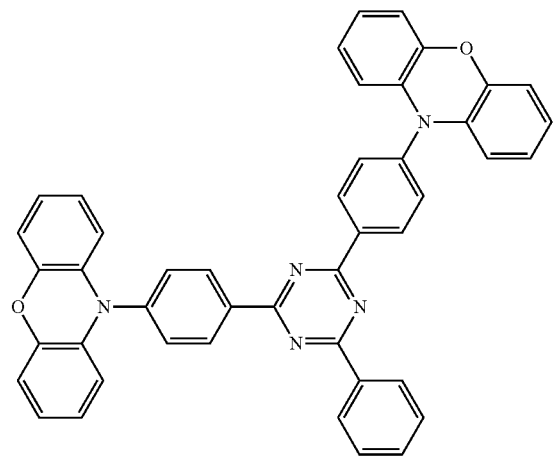
1-4
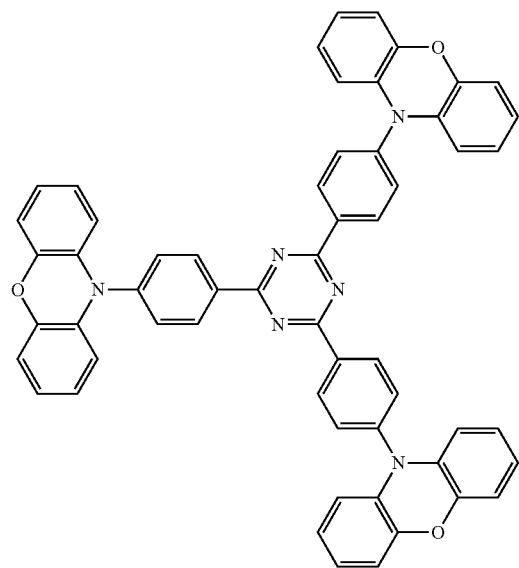
1-5
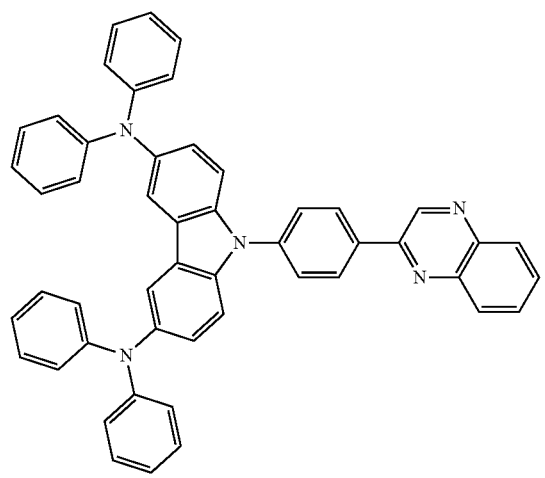
1-6

-continued
1-7
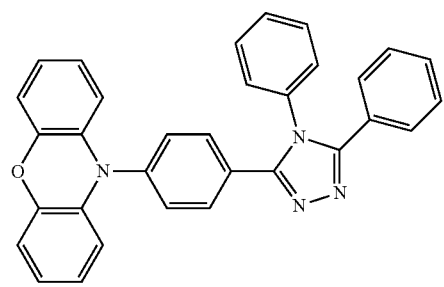
1-8
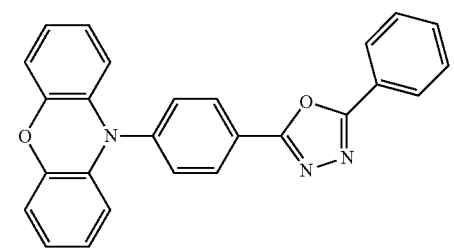
1-9
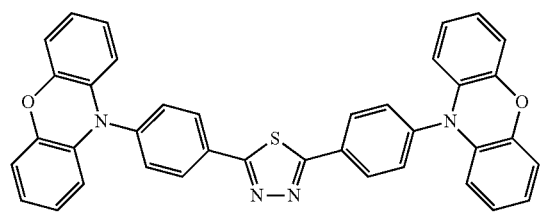
1-10
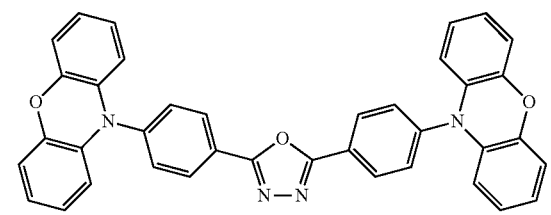
1-11
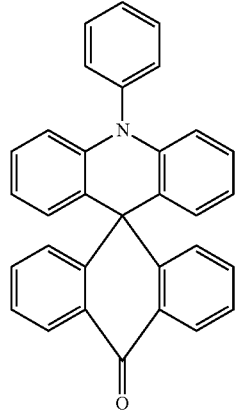
1-12
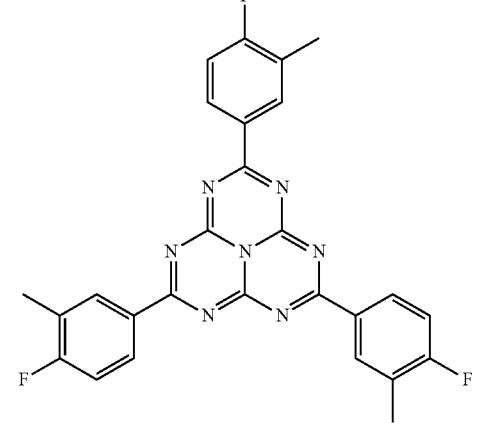
1-13
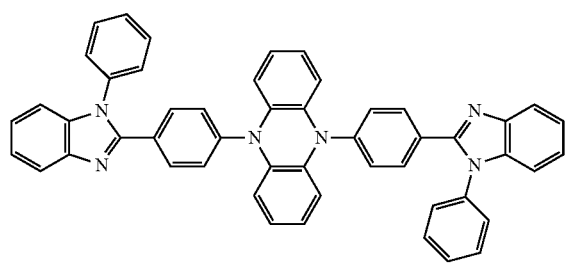
1-14
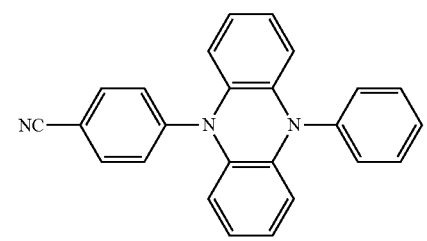
1-15
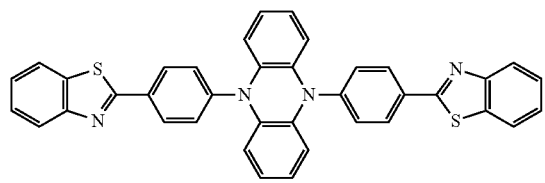
1-16
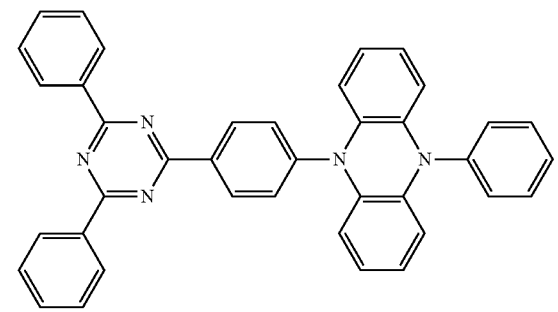

-continued
1-17
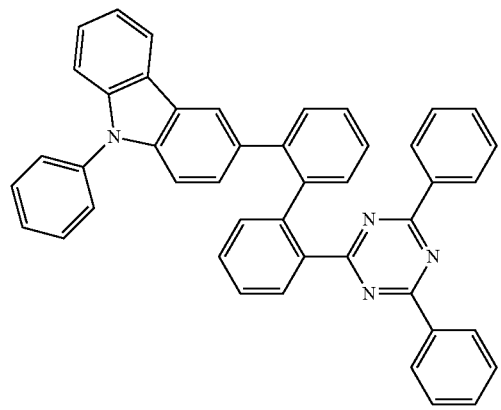
1-18
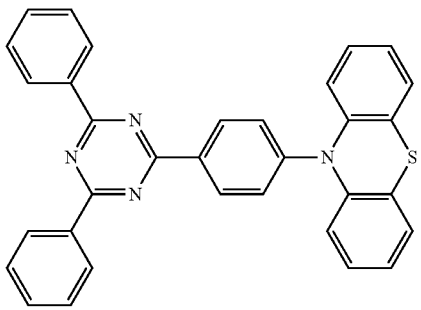
1-19
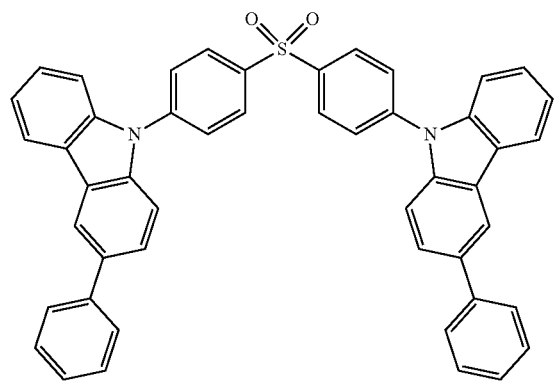
1-20
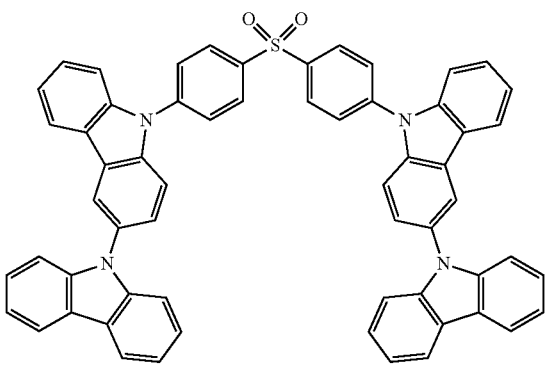
1-21
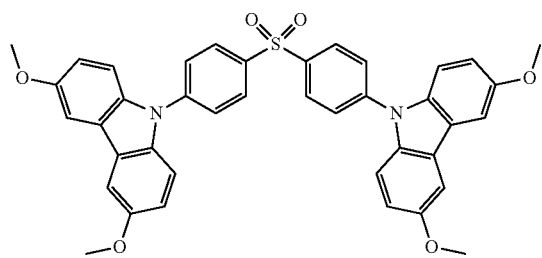
1-22
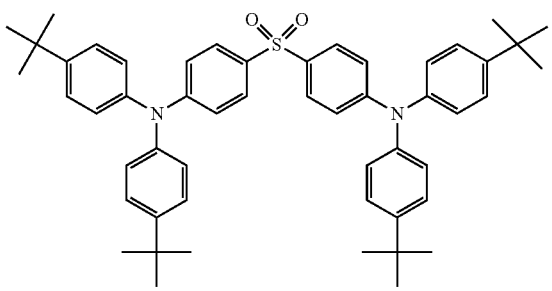
1-23
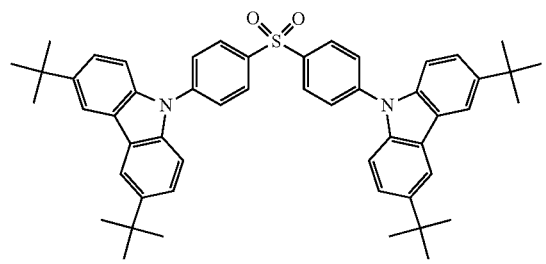
1-24
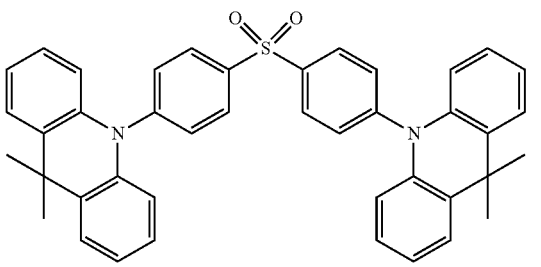
1-25
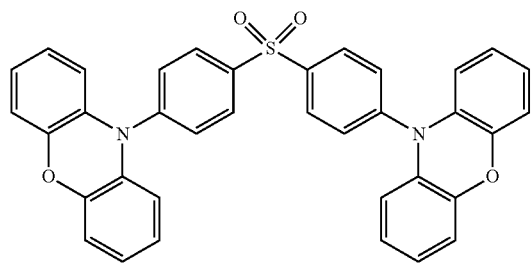
1-26

-continued
1-27
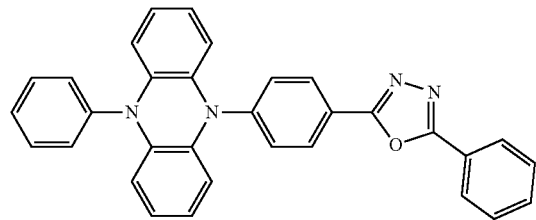
1-28
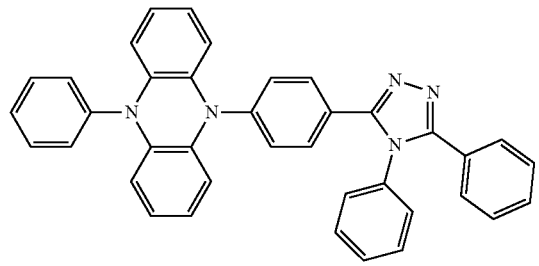
1-29
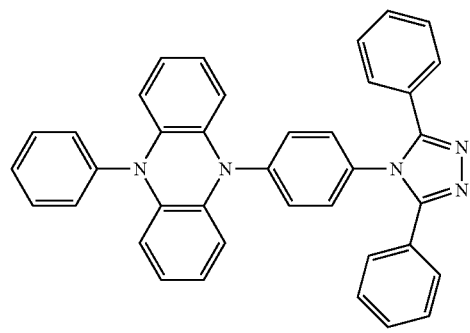
1-30
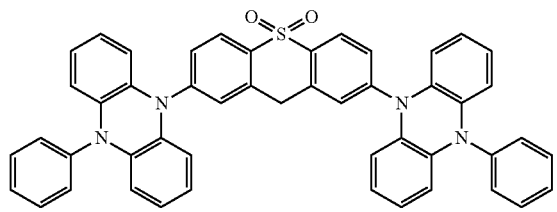
1-31
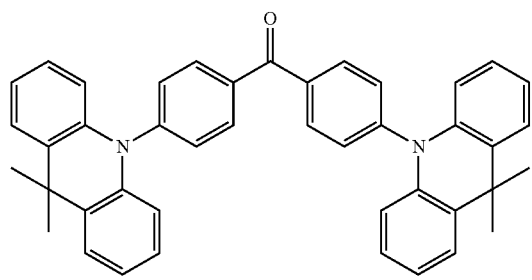
1-32
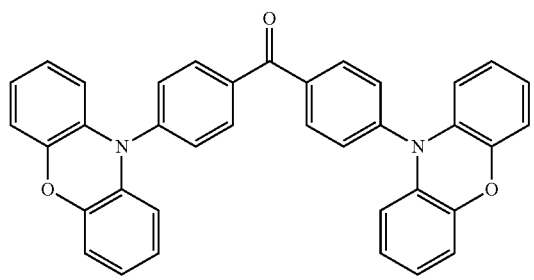
1-33
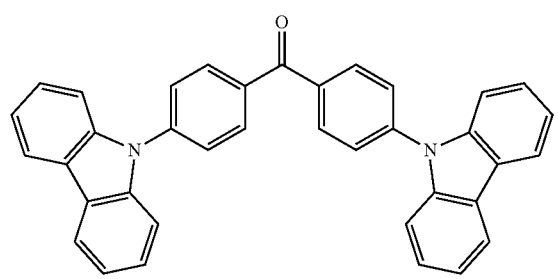
1-34
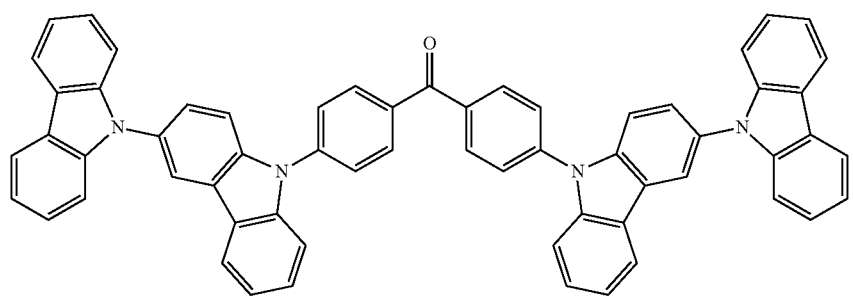

1-35
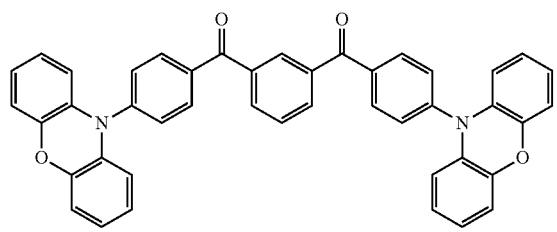
1-36
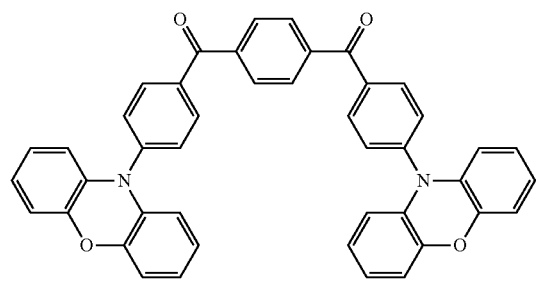
1-37
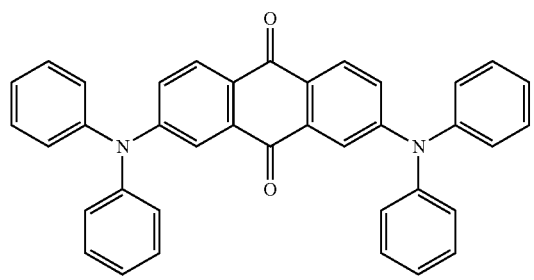
1-38
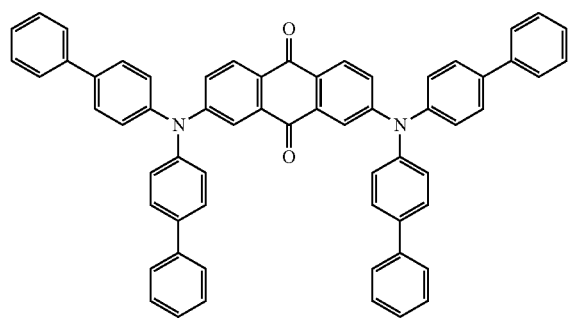
1-39
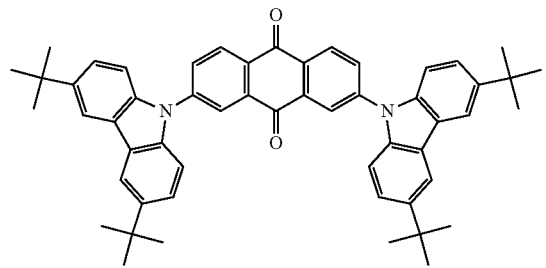
1-40
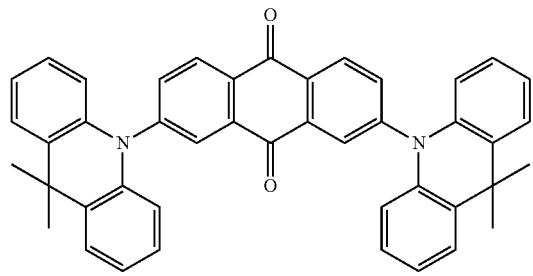
1-41
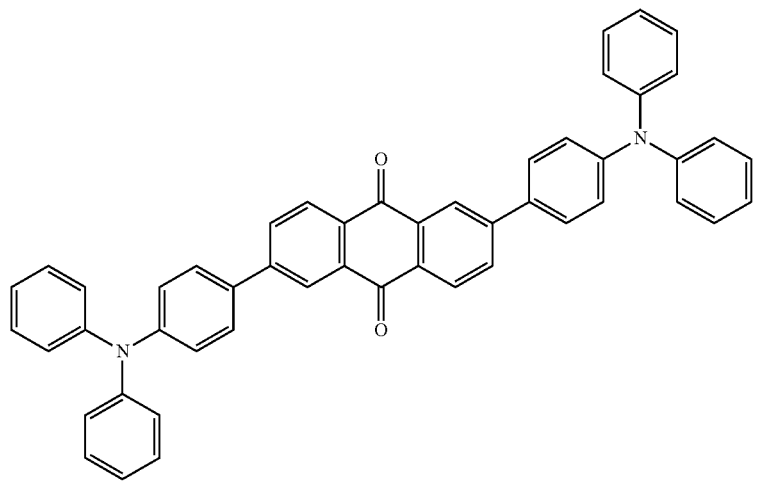

-continued
1-42
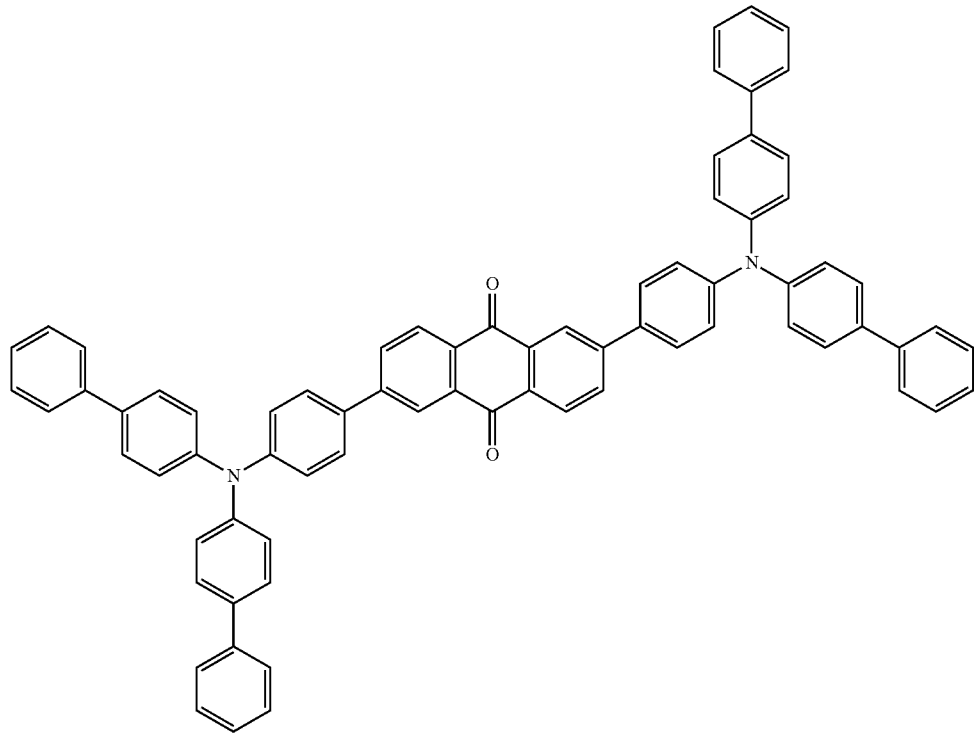
1-43
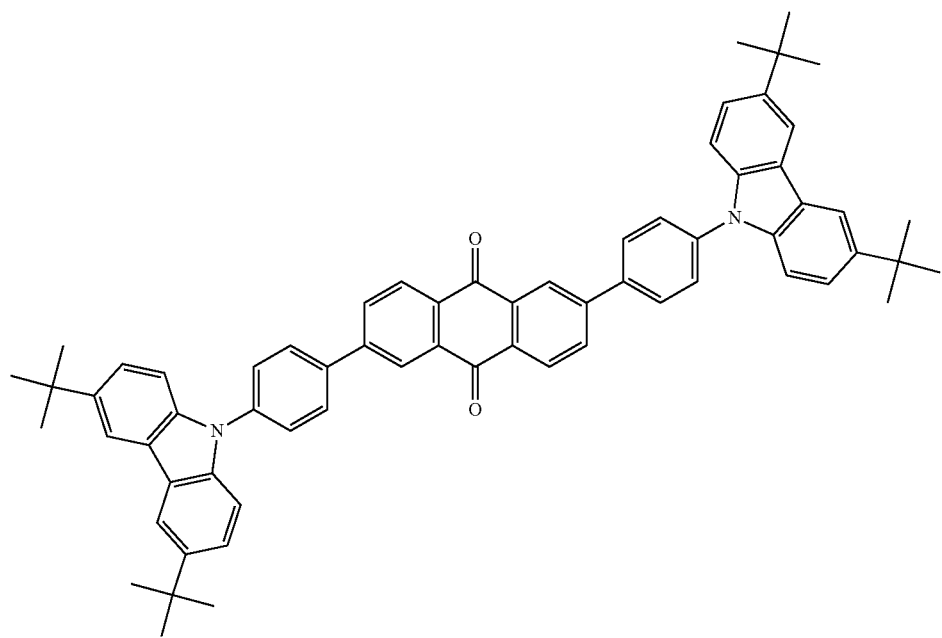

1-44
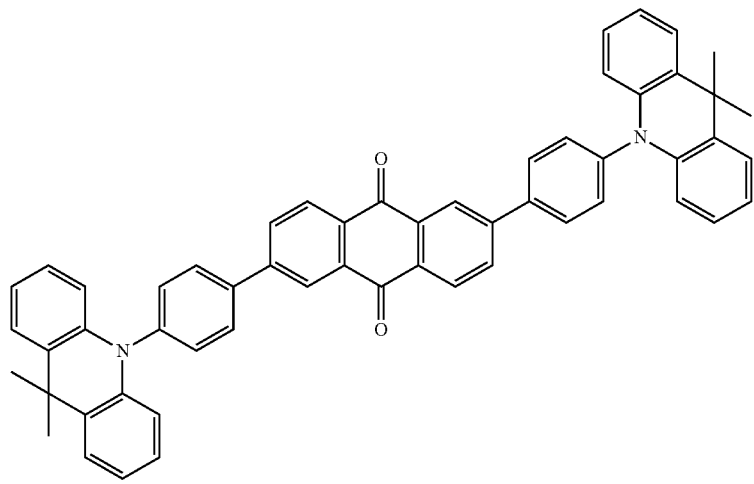
1-45
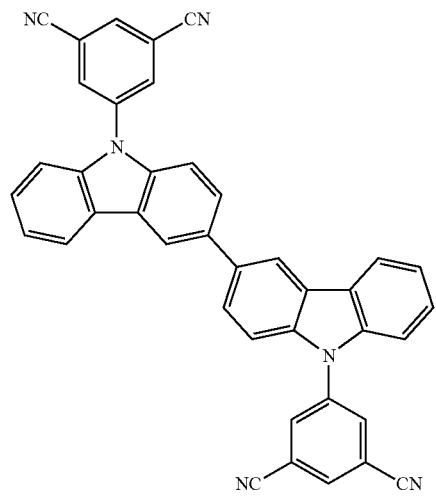
1-46
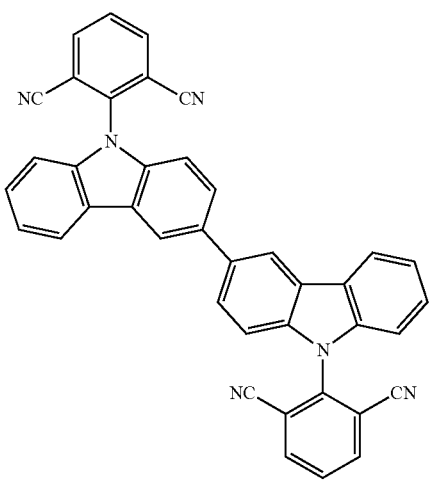
1-47
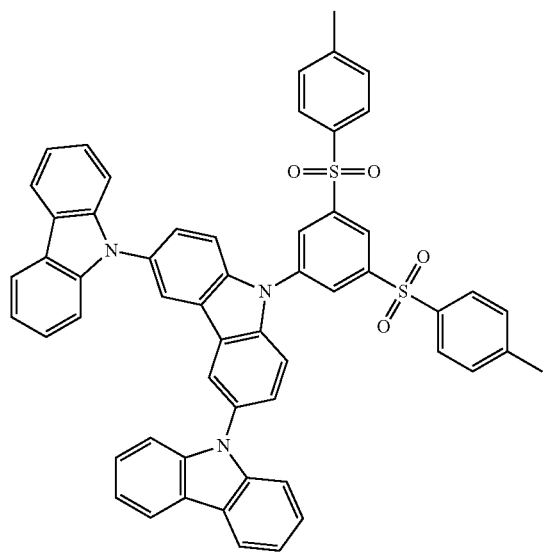
1-48
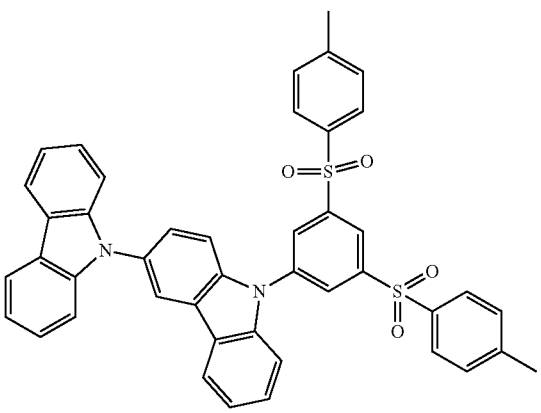

-continued
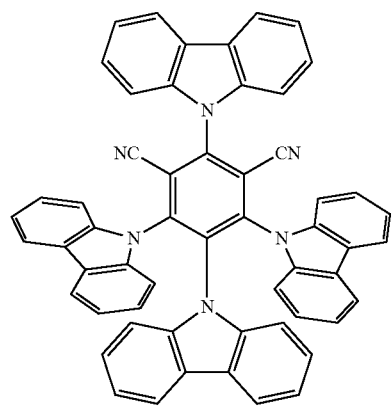
1-49
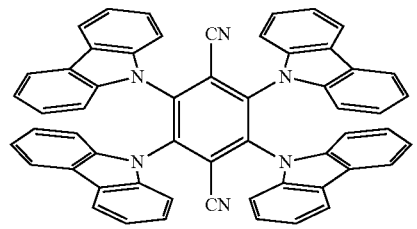
1-50
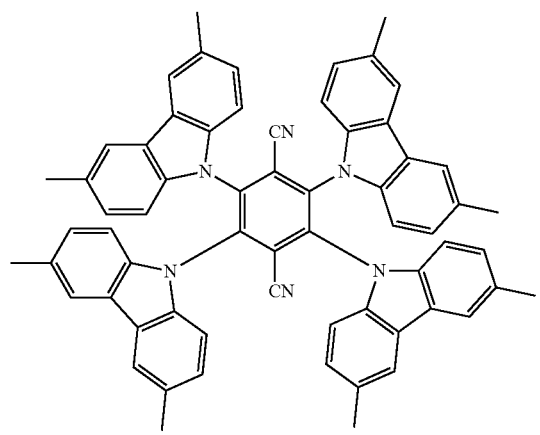
1-51
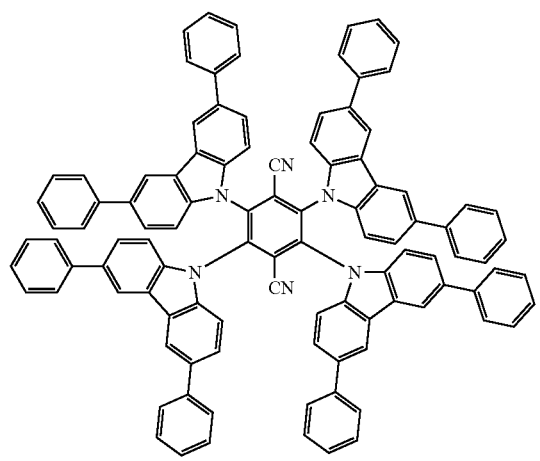
1-52
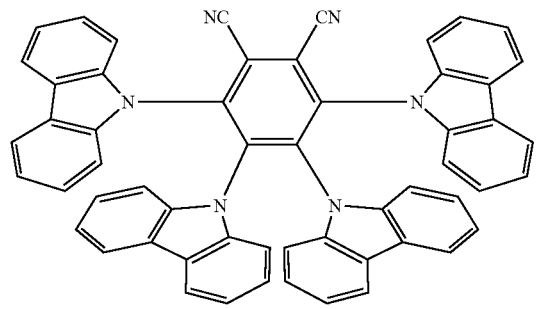
1-53
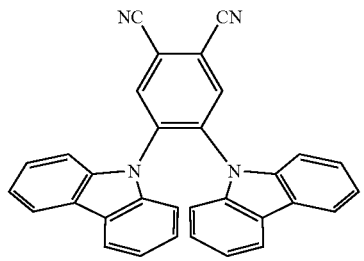
1-54

-continued
1-55
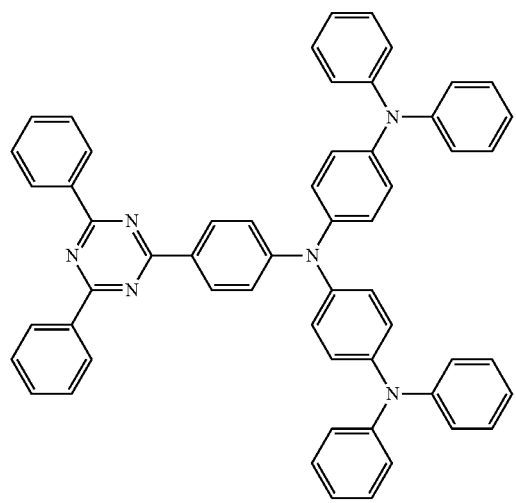
1-56
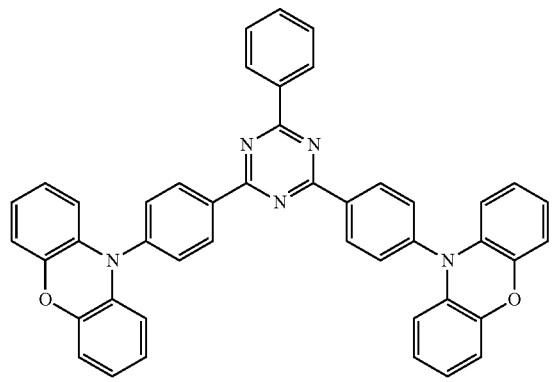
1-57
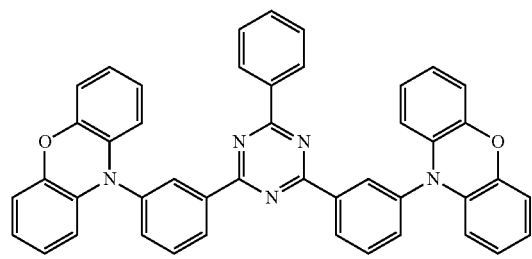
1-58
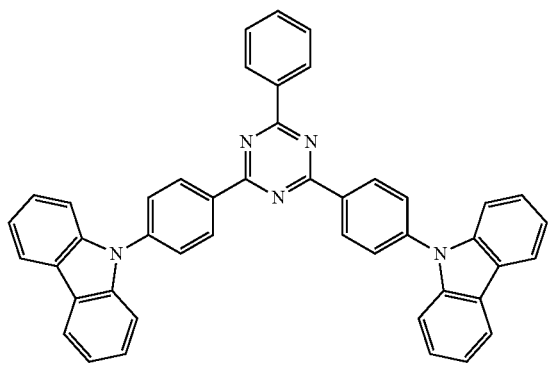
1-59
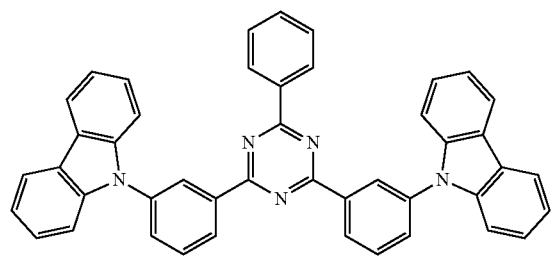
1-60
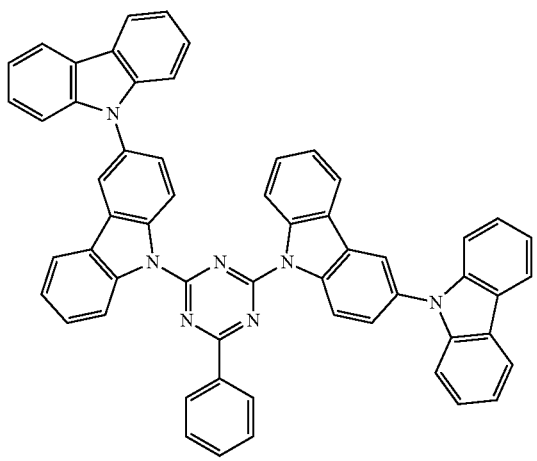

-continued
1-61
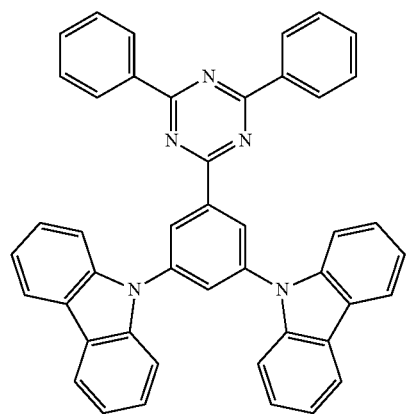
1-62
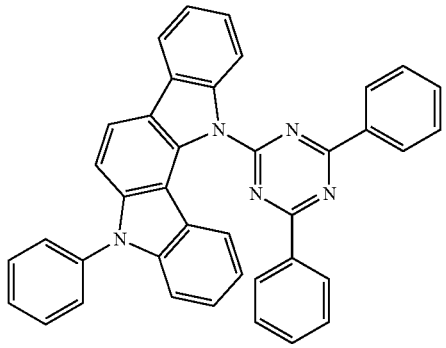
1-63
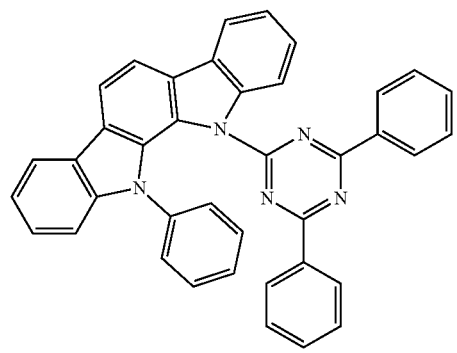
1-64
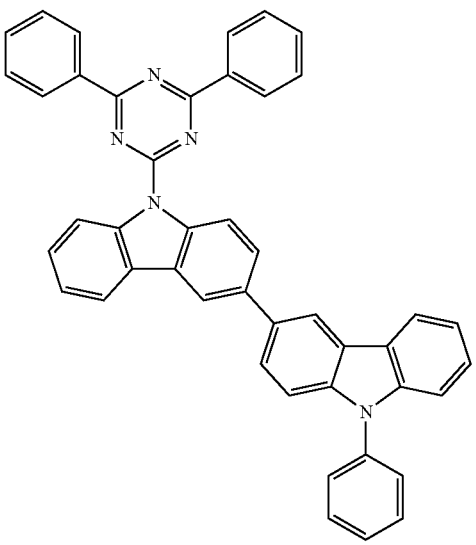
1-65
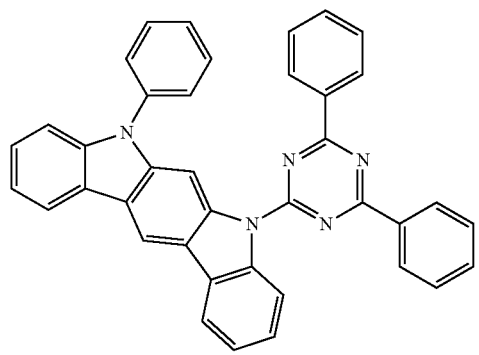
1-66
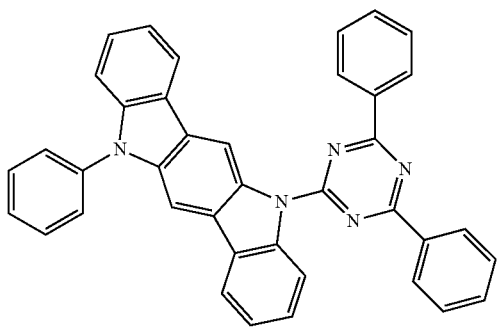

-continued
1-67
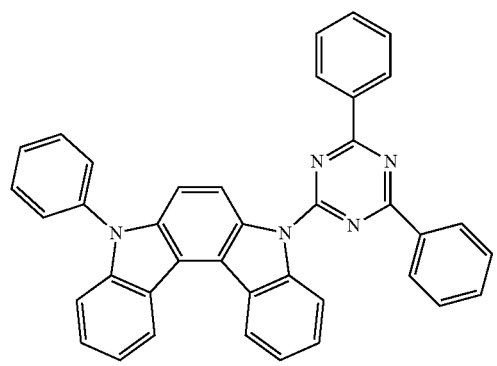
1-68
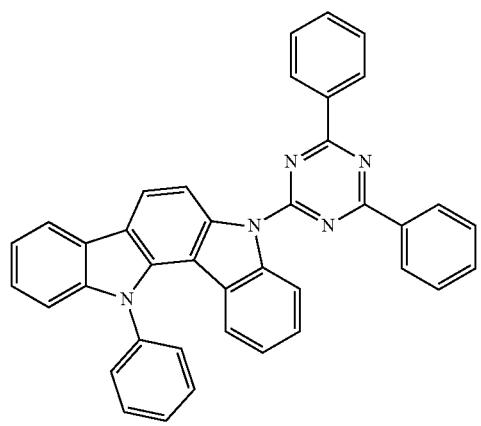
1-69
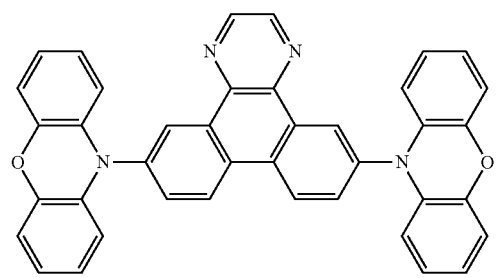
1-70
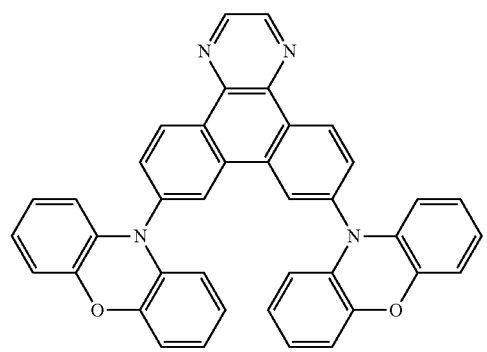
1-71
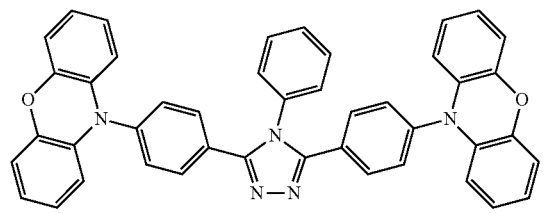
1-72
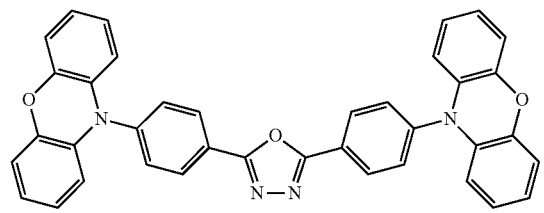

1-73
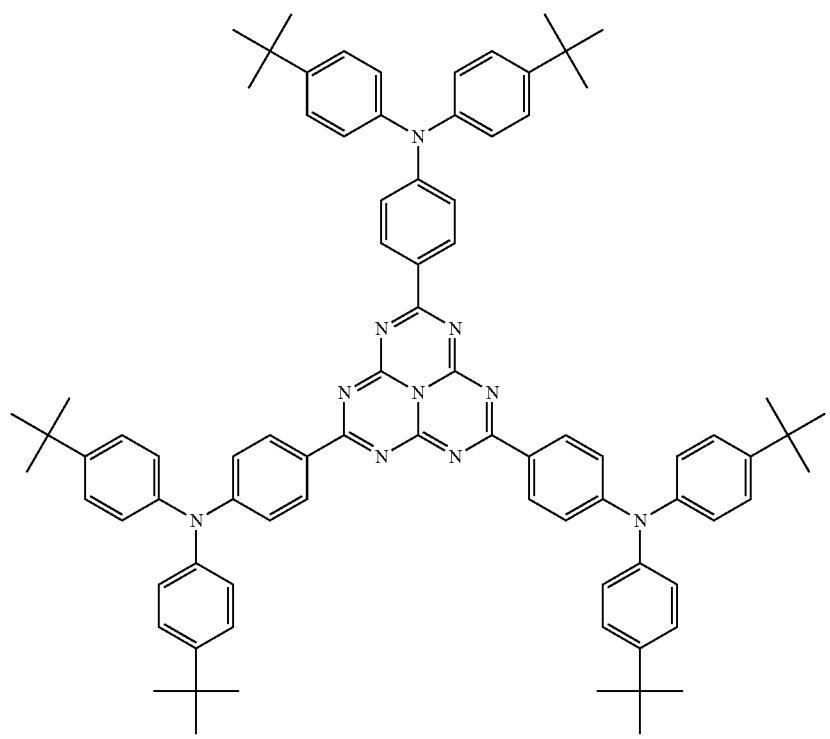
1-74 1-75
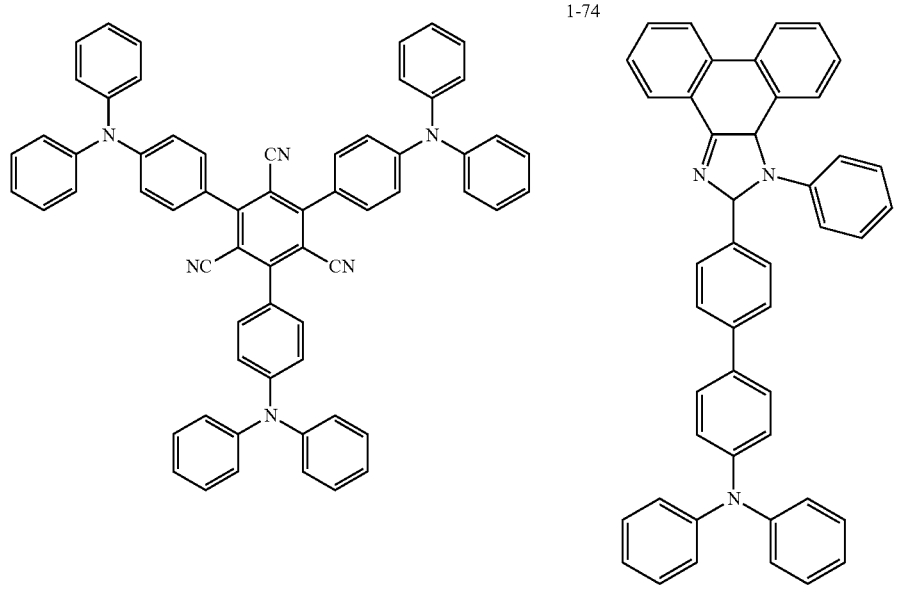

-continued
| | |
|---|---|
| 1-76 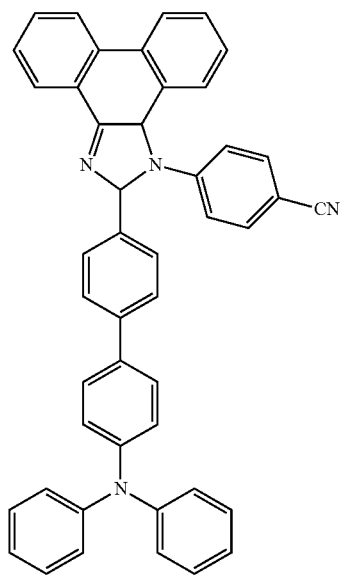 | 1-77 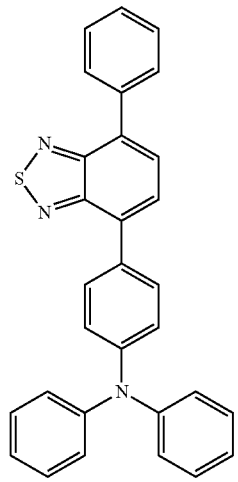 |
| 1-78 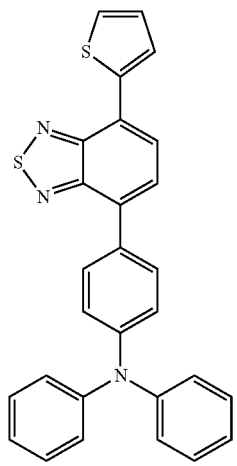 | 1-79 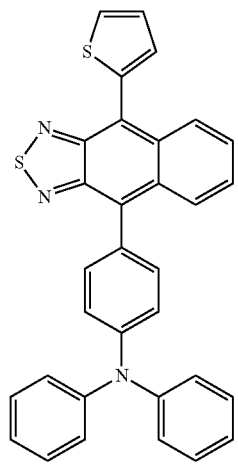 |
| 1-80 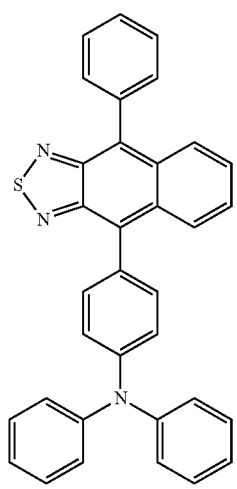 | 1-81 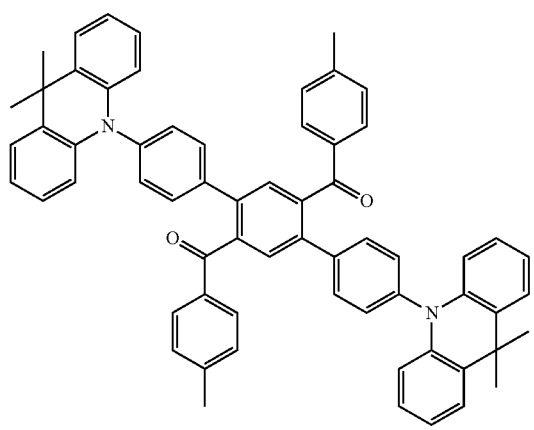 |

-continued
1-82
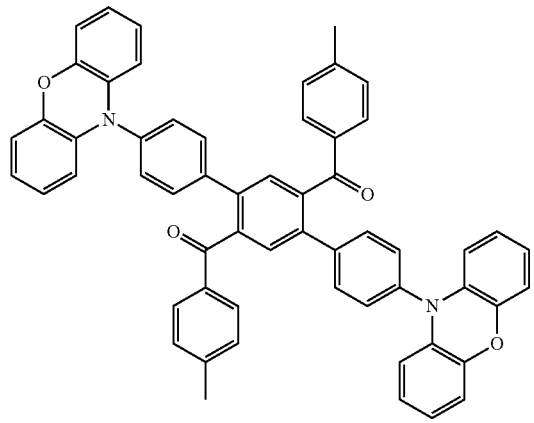
1-83
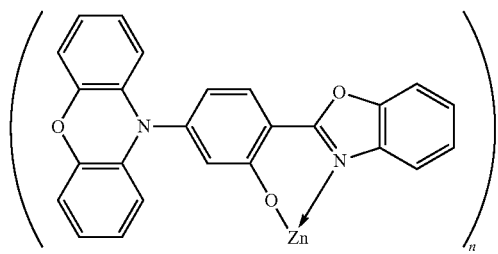
1-84
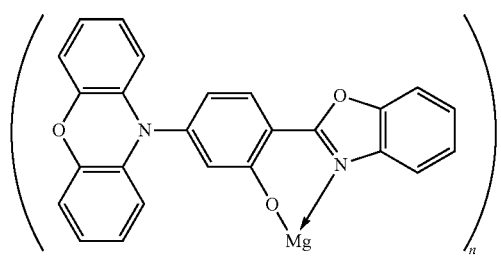
1-85
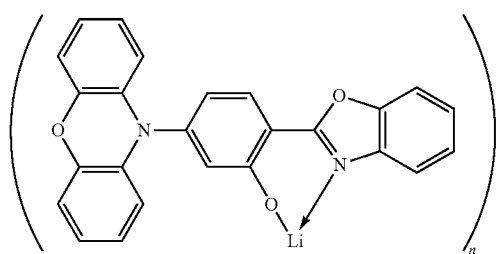
1-86
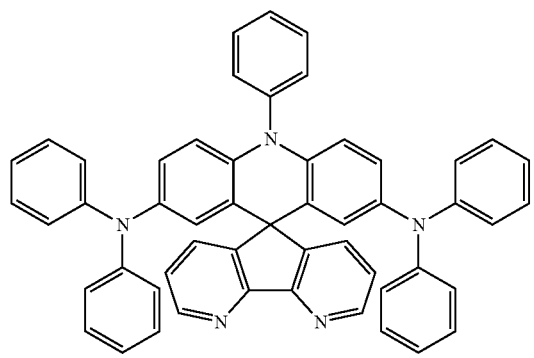
1-87
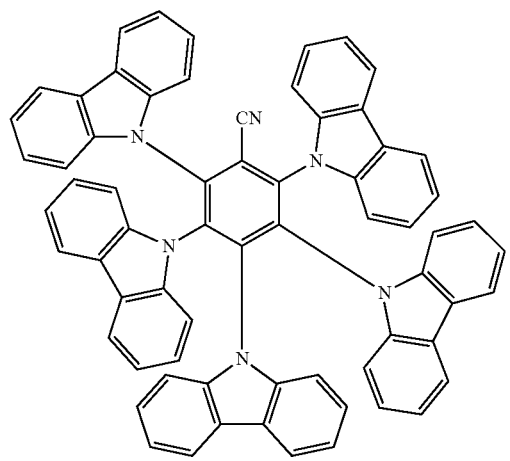

1-88
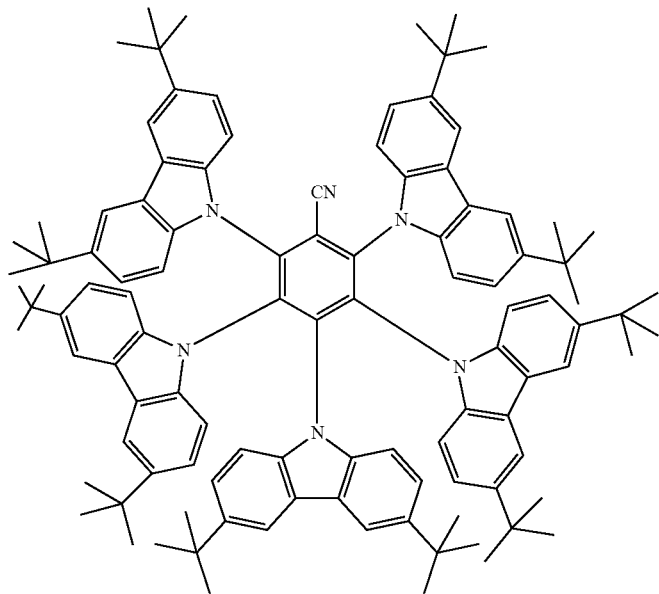
1-89
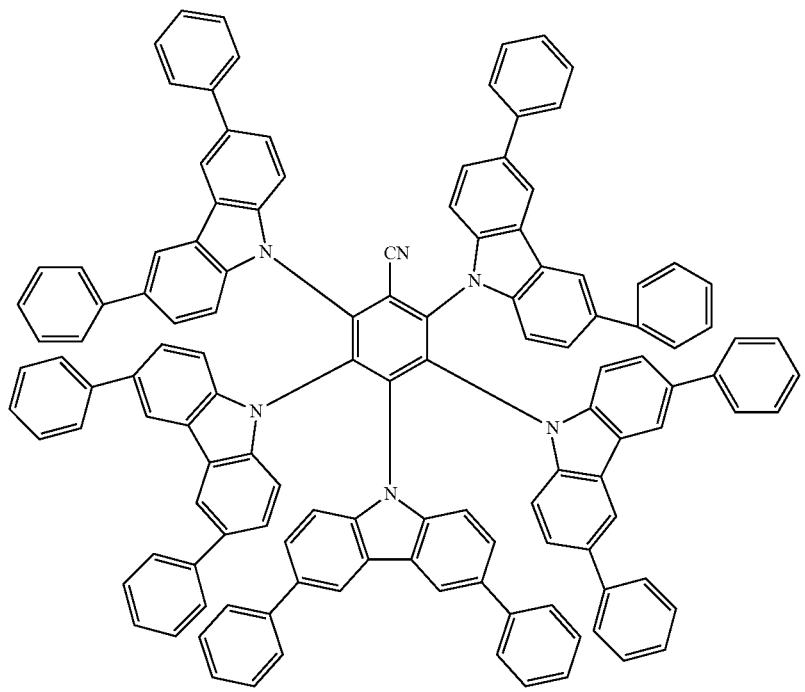

-continued
1-90
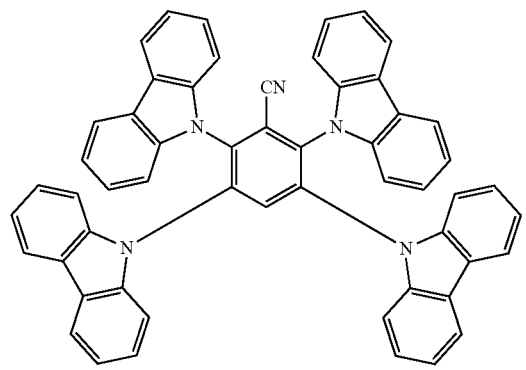
1-91
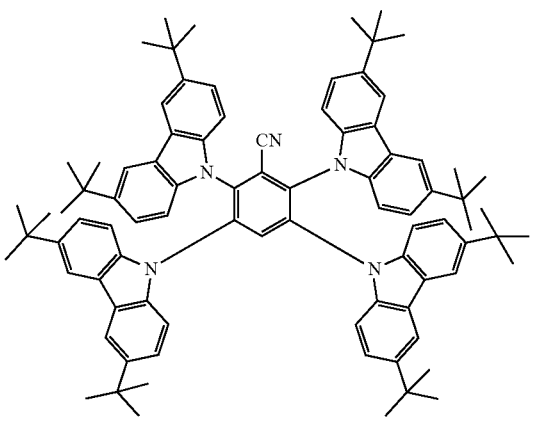
1-92
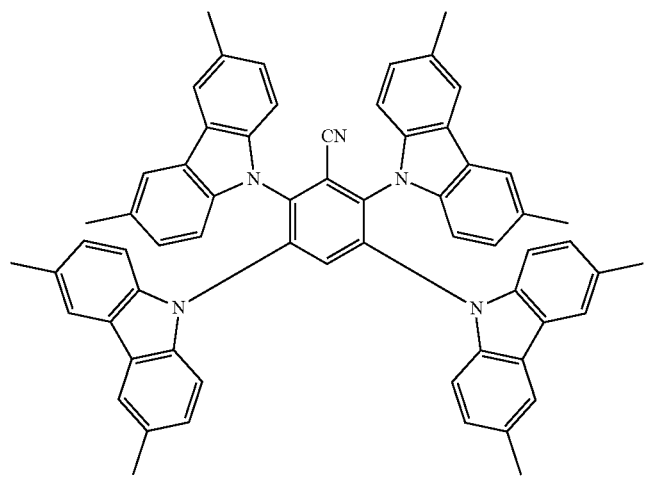
1-93
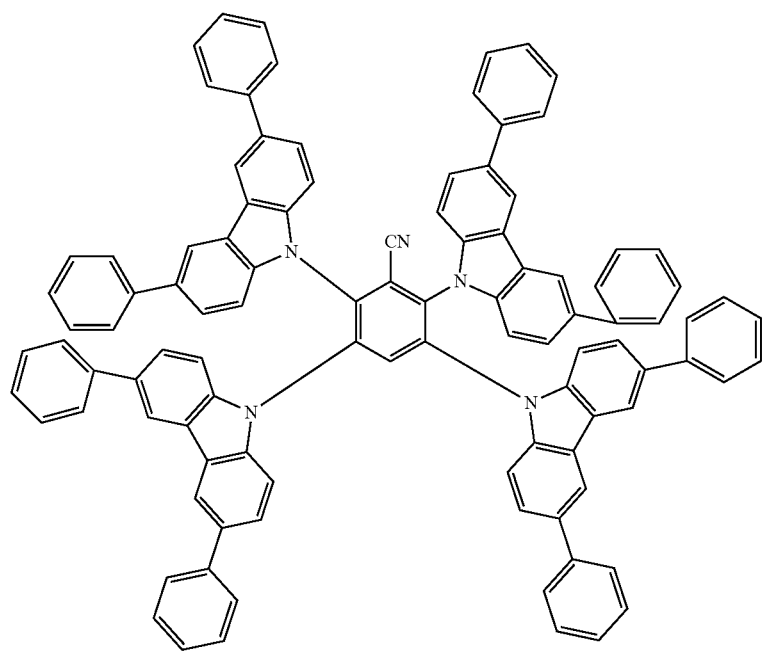

-continued
1-94
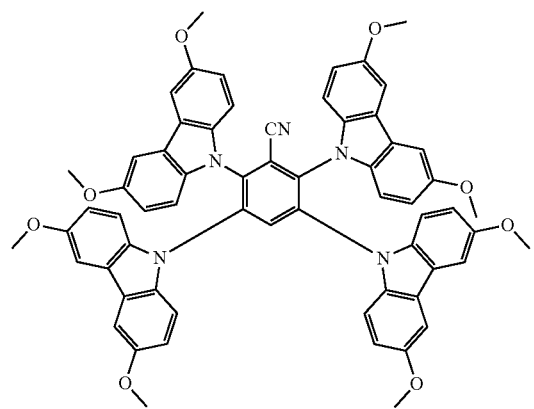
1-95
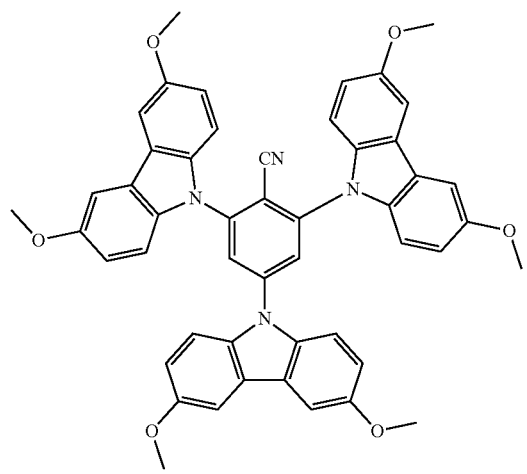
1-96
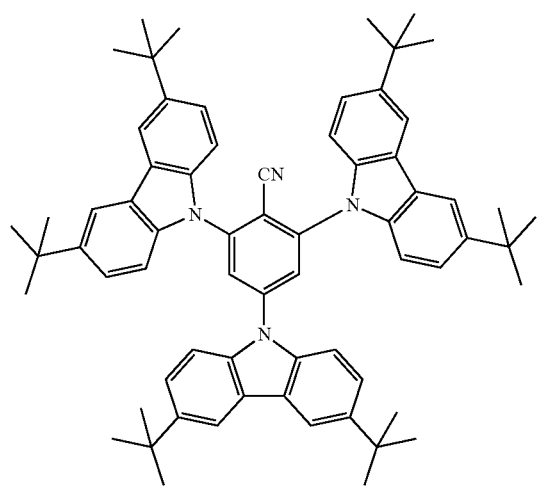
1-97
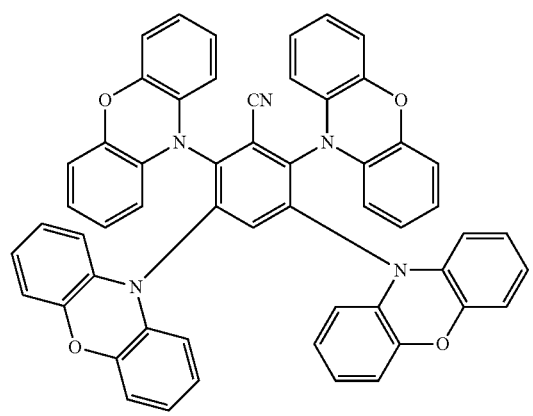
1-98
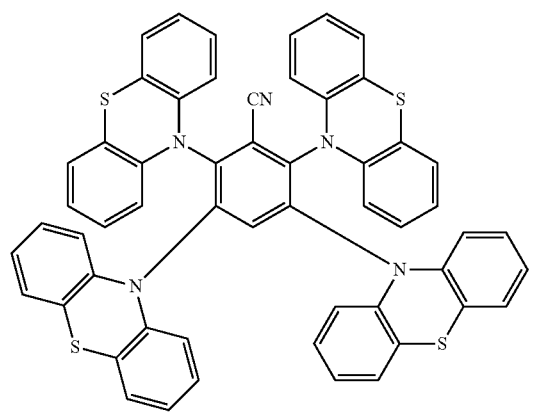
1-99
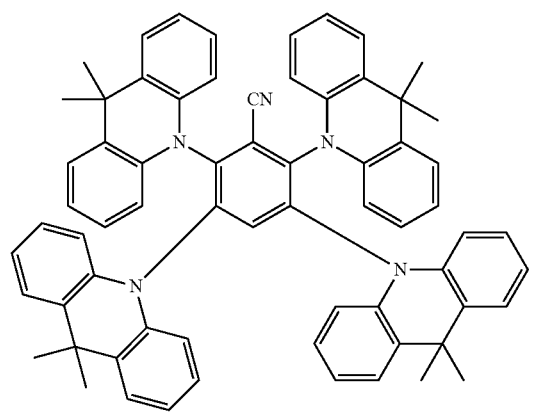

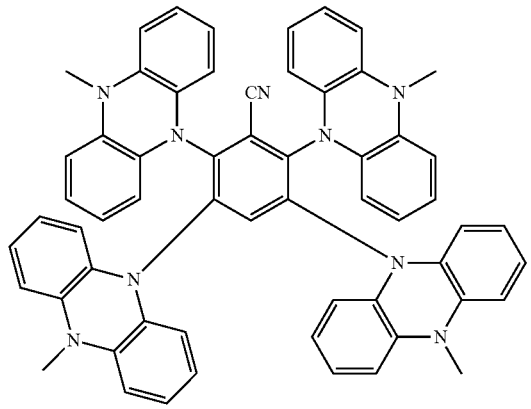

1-100

A preparation method of the aforementioned organic electroluminescent device comprises the following steps:
evaporation coating a first electrode layer, a light emitting layer and a second electrode layer in sequence on a substrate by using an open mask;
wherein, the light emitting layer is prepared by co-evaporation coating of a host material and a dye.

As compared to prior arts, the above-mentioned technical scheme of the present invention has the following advantages:

(1) The present invention aims to providing a single-layered device configuration, wherein the organic electroluminescent device only needs to consist of a first electrode layer, a light emitting layer and a second electrode layer, and the light emitting layer is prepared by co-evaporation coating of only a host material and a dye, without the necessity to prepare other organic layers such as a hole transport layer, a hole blocking layer, an electron transport layer or an electron blocking layer, so that the structure of the device is greatly simplified, the preparation process is shortened, and the production cost is reduced.

(2) In the present invention, the host material has $T_1$-$S_1$≤0.3 eV, such material has small difference between its singlet state energy level and its triplet state energy level, in particular, the host material may be a thermal activating delayed fluorescence material (TADF), or an exciplex made from an electron transport type material and a hole transport type material, or a composition made from a thermal activating delayed fluorescence material (TADF) and a hole transport type material, or a composition made from a thermal activating delayed fluorescence material (TADF) and an electron transport type material, these three types of compositions have donor groups and receptor groups, and therefore have capabilities to transport both holes and electrons. Meanwhile, the device configuration adopted by the present invention can sufficiently utilize the triplet state energy in the host material and the dye, because the difference between the singlet state energy level and the triplet state energy level is small, which is beneficial for injection of electrons and holes, so that the problem of low efficiency and short service life caused by exciton quenching can be solved. Therefore, the luminous efficiency can be increased and the service life of the device can be prolonged.

BRIEF DESCRIPTION OF THE DRAWINGS

In order to make the content of the present invention more easy to be understood clearly, hereinafter, the present invention is further described in detail according to specific embodiments of the present invention with reference to the accompanying drawings, wherein, The FIGURE is a structural schematic diagram of an organic electroluminescent device of the present invention.

DETAILED DESCRIPTION OF EMBODIMENTS

The present invention is further described hereinafter by illustrating specific embodiments.

The present invention can be implemented in many different forms, and should not be interpreted to be limited to the embodiments described herein. On the contrary, by providing these embodiments, the present disclosure is made complete and thorough, and the inventive concept of the present invention is sufficiently conveyed to those skilled in the art, wherein the present invention is defined by the Claims. In the accompanying drawings, for the sake of clarity, dimensions and relative sizes of layers and areas might be exaggerated. It should be understood that, when one element such as a layer, an area or a substrate plate is described as "formed on" or "configured on" another element, this one element may be configured directly upon that another element, or there may exist intermediate element(s). On the contrary, when one element is described as "directly formed upon" or "directly configured upon" another element, there exist no intermediate element.

As shown in the FIGURE, an organic electroluminescent device in the present invention comprises a substrate and light emitting units formed in sequence on the substrate, wherein, each of the light emitting units comprises a first electrode layer 1, a light emitting layer 2 and a second electrode layer 3; the light emitting layer comprises a host material and a dye; the host material is made of materials having both electron transport capability and hole transport capability; at least one material in the host material has a CT excited triplet state energy level $T_1$ greater than its n-π excited triplet state energy level $S_1$, and $T_1$-$S_1$≤ltoreq. 0.3 eV; or, at least one material in the host material has a CT excited triplet state energy level $T_1$ greater than its n-π excited triplet state energy level $S_1$, and $T_1$-$S_1$≥1 eV, with the difference between its n-π excited second triplet state energy level and its CT excited first singlet state energy level being in the range of −0.1 eV to 0.1 eV.

A thermal activating delayed fluorescence material is a material in which there exists charge transfer transition. Both donor group units and receptor group units exist simultaneously in a thermal activating delayed fluorescence material, which gives the thermal activating delayed fluorescence material both electron transport capability and hole transport capability, wherein, the donor group unit is one donor group or a group formed by two or more donor groups being connected together, the receptor group unit is one receptor group or a group formed by two or more receptor groups being connected together. In particular, the thermal activating delayed fluorescence material has a structure selected from the structural formulas (1-1) to (1-100).

The host material in the present invention may be an exciplex made from a single thermal activating delayed fluorescence material, or an exciplex made from an electron transport type material and a hole transport type material, or a composition made from a thermal activating delayed fluorescence material (TADF) and a hole transport type material, or a composition made from a thermal activating delayed fluorescence material (TADF) and an electron transport type material.

The electron transport type material is tri-(8-oxyquinoline)-aluminum, 2,9-dimethyl-4,7-diphenyl-1,10-o-phenanthroline, 4,7-diphenyl-1,10-o-phenanthroline, di-(2-methyl-8-quinolyl)-4-phenyl-phenoxide-aluminum(III), 1,3,5-tri-(1-phenyl-1H-benzimidazole-2-yl)-benzene, or 1,3,5-tri-[(3-pyridyl)-3-phenyl]-benzene.

| Abbreviation | Full name | Structural formula |
| --- | --- | --- |
| Alq3 | tri-(8-oxyquinoline)-aluminum | |
| BCP | 2,9-dimethyl-4,7-diphenyl-1,10-o-phenanthroline | |
| Bphen | 4,7-diphenyl-1,10-o-phenanthroline | |
| BAlq | di-(2-methyl-8-quinolyl)-4-phenyl-phenoxide-aluminum(III) | |

-continued

| Abbreviation | Full name | Structural formula |
|---|---|---|
| TPBi | 1,3,5-tri-(1-phenyl-1H-benzimidazole-2-yl)-benzene | |
| TmPyPB | 1,3,5-tri-[(3-pyridyl)-3-phenyl]-benzene | |

The hole transport type material is N,N'-di-(1-naphthyl)-N,N'-diphenyl-1,1'-biphenyl-4,4'-diamine, N,N'-diphenyl-N,N'-di-(m-methyl-phenyl)-1,1'-biphenyl-4,4'-diamine, 4,4'-cyclohexyl-di-[N,N-di-(4-methyl-phenyl)]-phenylamine, 4,4'-N,N'-di-carbazole-biphenyl, 4,4',4"-tri-(carbazole-9-yl)-triphenylamine, or 1,3-di-(carbazole-9-yl)-benzene.

| Abbreviation | Full name | Structural formula |
|---|---|---|
| NPB | N,N'-di-(1-naphthyl)-N,N'-diphenyl-1,1'-biphenyl-4,4'-diamine | |
| TPD | N,N'-diphenyl-N,N'-di-(m-methyl-phenyl)-1,1'-biphenyl-4,4'-diamine | |

-continued

| Abbreviation | Full name | Structural formula |
|---|---|---|
| TAPC | 4,4'-cyclohexyl-di-[N,N-di-(4-methyl-phenyl)]-phenylamine | |
| CBP | 4,4'-N,N'-di-carbazole-biphenyl | |
| TCTA | 4,4',4''-tri-(carbazole-9-yl)-triphenylamine | |
| mCP | 1,3-di-(carbazole-9-yl)-benzene | |

The red dye used in the present invention is selected from the following structural formulas:
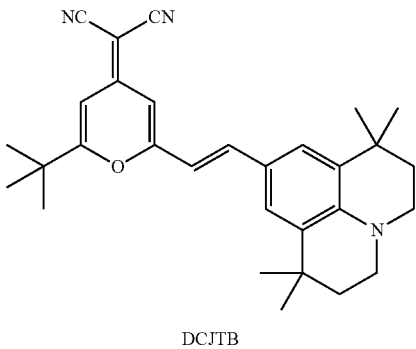
DCJTB
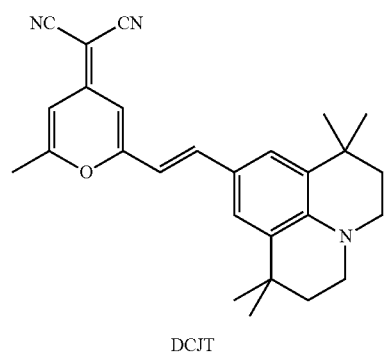
DCJT
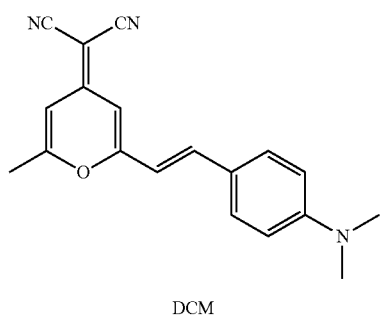
DCM
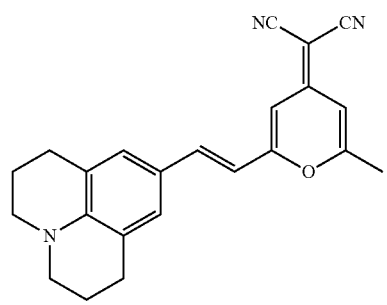
DCM2
-continued
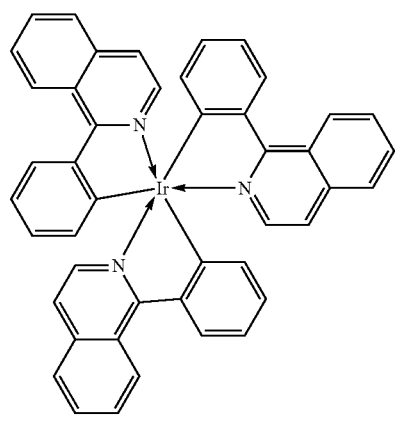
Ir(piq)$_3$
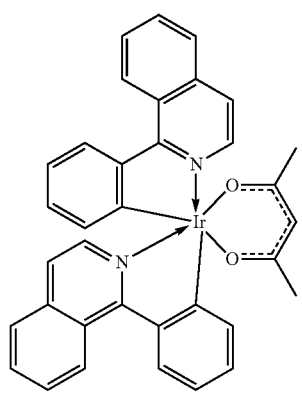
Ir(piq)$_2$(acac)
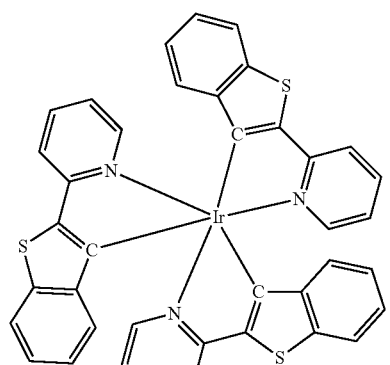
Ir(btpy)$_3$
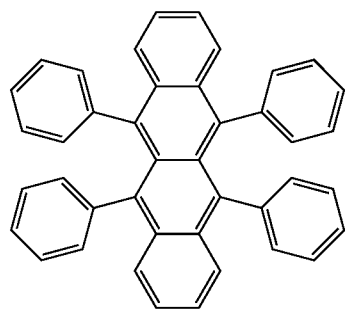
Rubrene

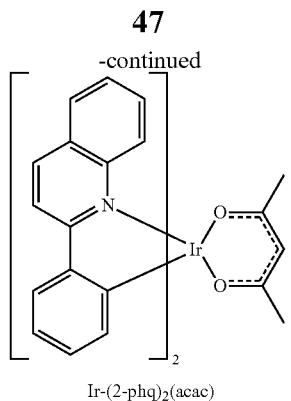
Ir-(2-phq)₂(acac)
The green dye used in the present invention is selected from the following structural formulas:
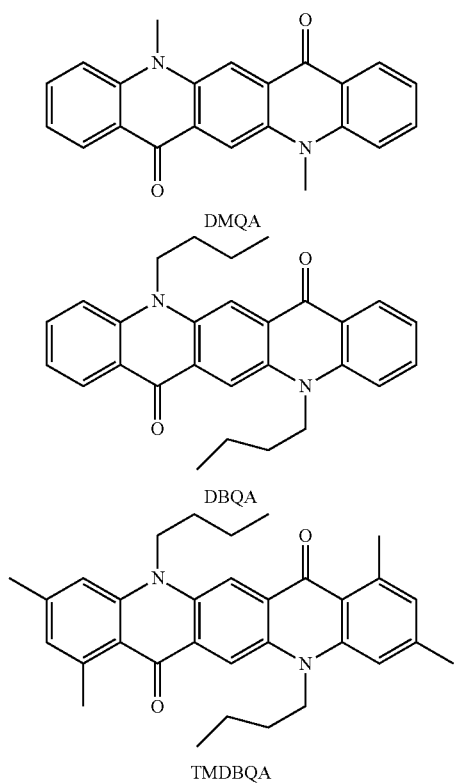
DMQA
DBQA
TMDBQA
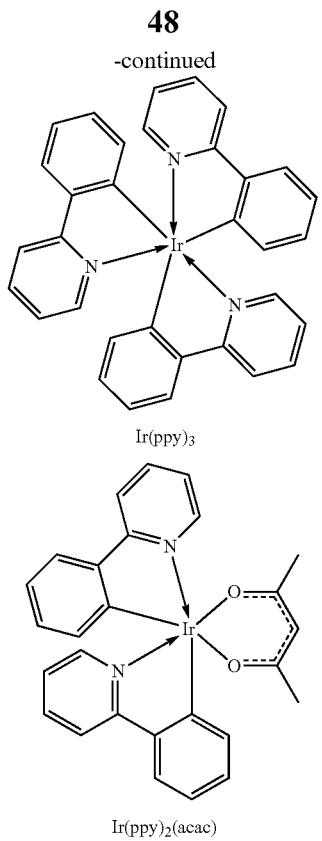
Ir(ppy)₃
Ir(ppy)₂(acac)
Ir(mppy)₃
The blue dye used in the present invention is selected from the following structural formulas:
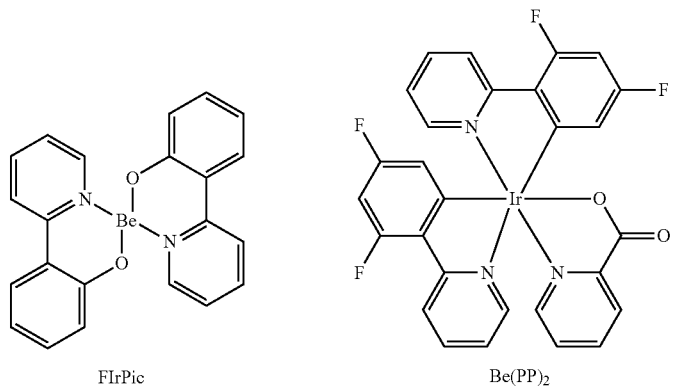
FIrPic
Be(PP)₂

-continued

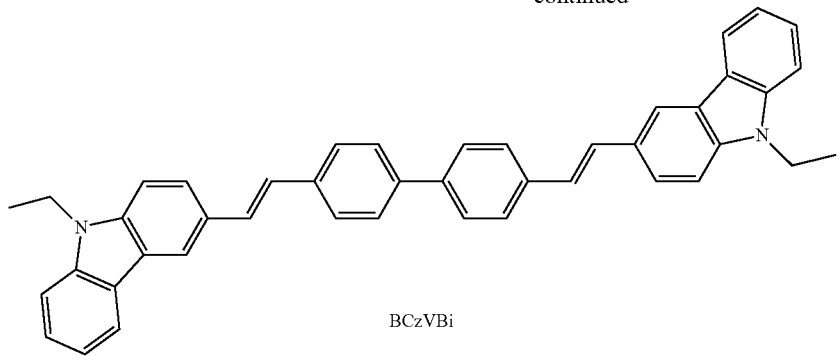

BCzVBi

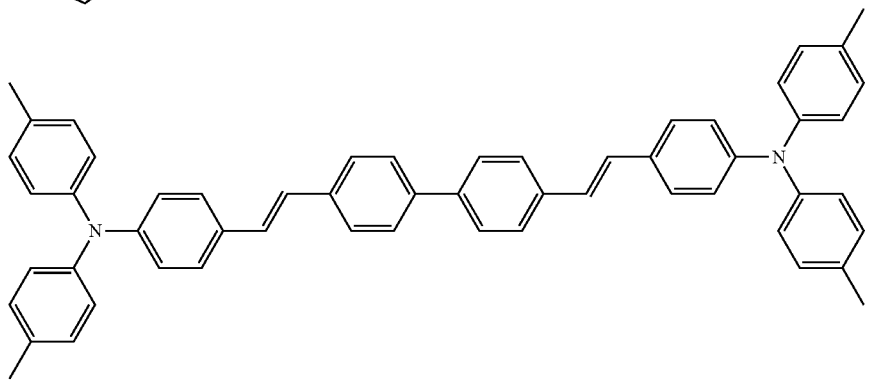

DPAVBi

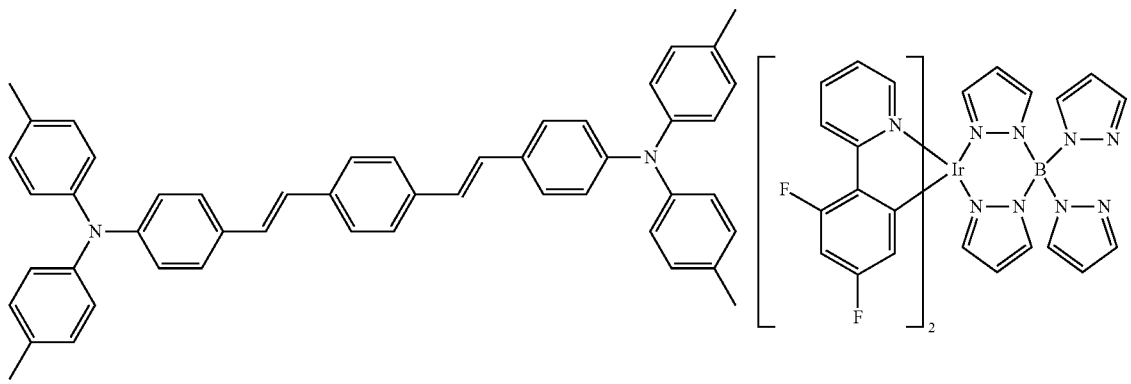

DPAVB                                    FIr6

Embodiment 1

A device 1 of this embodiment has the following structure:

glass/ITO/(1-24):CBP:Ir(piq)$_2$(acac)(5%)/cathode

The device 1 consists of a substrate, an anode layer, a light emitting layer and a cathode layer, without any hole injection layer, hole transport layer, electron injection layer or electron transport layer. The host material of the light emitting layer is made from the thermal activating delayed fluorescence material of the formula (1-24) and the hole transport type material of CBP, at a mass ratio of 1:1.

The preparation method of the device 1 is as follows: evaporation coating an anode layer (ITO), a light emitting layer and a cathode layer (cathode) in sequence on a substrate by using an open mask, wherein the light emitting layer is prepared by co-evaporation coating of a host material (1-24):CBP and a dye Ir(piq)$_2$(acac), the doping concentration of the dye Ir(piq)$_2$(acac) is 5 wt %.

Embodiment 2

A device 2 of this embodiment has the following structure:

glass/ITO/(1-88):BAlq:Ir(piq)$_2$(acac)(5%)/cathode

In the device 2, the host material of the light emitting layer is made from an electron transport type material and the thermal activating delayed fluorescence material of the formula (1-88), at a mass ratio of 1:1. Herein, the thermal activating delayed fluorescence material serves as a hole transport type material.

The preparation method of the device 2 comprises the steps of evaporation coating an anode layer (ITO), a light emitting layer and a cathode layer (cathode) in sequence on a substrate by using an open mask, wherein the light emitting layer is prepared by co-evaporation coating of a host material (1-88):BAlq and a dye Ir(piq)$_2$(acac), the doping concentration of the dye Ir(piq)$_2$(acac) is 5 wt %.

Embodiment 3

A device 3 of this embodiment has the following structure:

glass/ITO/(1-88):(1-24):Ir(piq)$_2$(acac)(5%)/cathode

In the device 3, the host material of the light emitting layer is an exciplex made from an electron transport type thermal activating delayed fluorescence material and a hole transport type thermal activating delayed fluorescence material), at a mass ratio of 1:1.

The preparation method of the device 3 is as follows: evaporation coating an anode layer (ITO), a light emitting layer and a cathode layer (cathode) in sequence on a substrate by using an open mask, wherein the light emitting layer is prepared by co-evaporation coating of a host material (1-88):(1-24) and a dye Ir(piq)$_2$(acac), the doping concentration of the dye Ir(piq)$_2$(acac) is 5 wt %.

Comparison Example 1

A comparison device 1 of this example has the following structure:

glass/ITO/HIL/HTL/CBP:Ir(piq)$_2$(acac)(5%)/HBL/ETL/cathode

Comparison Example 2

A comparison device 2 of this example has the following structure:

glass/ITO/HIL/HTL/BAlq:Ir(piq)$_2$(acac)(20%)/HBL/ETL/cathode

Comparison Example 3

A comparison device 3 of this example has the following structure:

glass/ITO/HIL/HTL/CBP:BAlq:Ir(piq)$_2$(acac)(5%)/HBL/ETL/cathode

TABLE 1

| Device | Brightness (cd/m$^2$) | Luminous efficiency (cd/A) | External quantum efficiency (%) | Service life T$_{90}$ (hrs) |
| --- | --- | --- | --- | --- |
| Device 1 | 5000 | 22 | 24 | 500 |
| Device 2 | 5000 | 25 | 23 | 625 |
| Device 3 | 5000 | 29 | 26 | 648 |
| Comparison device 1 | 5000 | 13 | 15 | 430 |
| Comparison device 2 | 5000 | 16 | 16 | 472 |
| Comparison device 3 | 5000 | 19 | 16 | 498 |

Embodiments 4-12

Devices 4-12 of these embodiments have the following structure:

glass/ITO/TADF:hole transport type material:fluorescence material/cathode

Wherein, the respective materials and mass ratios of the TADF, the hole transport type material and the fluorescence material are listed in Table 2.

Wherein the doping concentration of the fluorescence material refers to the ratio that the fluorescence material accounts for in the total mass of the light emitting layer, that is, the fluorescence material doping concentration=the fluorescence material mass/(the fluorescence material mass+the TADF mass+the hole transport type material mass)*100%.

The preparation method of the devices 4-12 comprises the step of evaporation coating an anode layer (ITO), a light emitting layer and a cathode layer (cathode) in sequence on a substrate by using an open mask, wherein the light emitting layer is prepared by co-evaporation coating of a host material (TADF:hole transport type material) and a fluorescence material.

TABLE 2

| | TADF | Hole transport type material | Mass ratio | fluorescence material | doping concentration of the fluorescence material |
| --- | --- | --- | --- | --- | --- |
| Device 4 | Formula (1-1) | NPB | 1:9 | DCJT | 15 wt % |
| Device 5 | Formula (1-2) | TCTA | 2:8 | BCzVBi | 15 wt % |
| Device 6 | Formula (1-3) | CBP | 3:7 | DPAVBi | 5 wt % |
| Device 7 | Formula (1-4) | mCP | 4:5 | BCzVBi | 5 wt % |
| Device 8 | Formula (1-5) | TPD | 5:4 | DCJT | 5 wt % |
| Device 9 | Formula (1-6) | TAPC | 6:3 | DCJT | 5 wt % |
| Device 10 | Formula (1-11) | CBP | 7:2 | BCzVBi | 5 wt % |
| Device 11 | Formula (1-15) | mCP | 8:1 | DPAVBi | 5 wt % |
| Device 12 | Formula (1-20) | mCP | 9:1 | BCzVBi | 5 wt % |

Embodiments 13-30

Devices 13-30 of these embodiments have the following structure:

glass/ITO/TADF:electron transport type material:fluorescence material/cathode

Wherein, the respective materials and mass ratios of the TADF, the electron transport type material and the fluorescence material are listed in Table 3.

Wherein the doping concentration of the fluorescence material refers to the ratio that the fluorescence material accounts for in the total mass of the light emitting layer, that is, the fluorescence material doping concentration=the fluorescence material mass/(the fluorescence material mass+the TADF mass+the electron transport type material mass)*100%.

The preparation method of the devices 13-30 comprises the step of evaporation coating an anode layer (ITO), a light emitting layer and a cathode layer (cathode) in sequence on a substrate by using an open mask, wherein the light emitting layer is prepared by co-evaporation coating of a host material (TADF:electron transport type material) and a fluorescence material.

TABLE 3

| | TADF | Electron transport type material | Mass ratio | fluorescence material | doping concentration of the fluorescence material |
| --- | --- | --- | --- | --- | --- |
| Device 13 | Formula (1-21) | TmPyPB | 1:9 | DCJT | 5 wt % |
| Device 14 | Formula (1-22) | TPBi | 2:8 | BCzVBi | 5 wt % |
| Device 15 | Formula (1-23) | BCP | 3:7 | DPAVBi | 5 wt % |
| Device 16 | Formula (1-24) | Bphen | 4:5 | BCzVBi | 5 wt % |

TABLE 3-continued

|  | TADF | Electron transport type material | Mass ratio | fluorescence material | doping concentration of the fluorescence material |
|---|---|---|---|---|---|
| Device 17 | Formula (1-25) | BCP | 5:4 | DCJT | 5 wt % |
| Device 18 | Formula (1-26) | Alq3 | 6:3 | BCzVBi | 5 wt % |
| Device 19 | Formula (1-31) | Bphen | 7:2 | DPAVBi | 5 wt % |
| Device 20 | Formula (1-35) | BCP | 8:1 | BCzVBi | 5 wt % |
| Device 21 | Formula (1-40) | BAlq | 9:1 | DCJT | 5 wt % |
| Device 22 | Formula (1-45) | Alq3 | 1:9 | DCM | 5 wt % |
| Device 23 | Formula (1-48) | BAlq | 2:8 | DMQA | 15 wt % |
| Device 24 | Formula (1-50) | TPBi | 3:7 | TMDBQA | 15 wt % |
| Device 25 | Formula (1-51) | Bphen | 4:5 | DPAVB | 5 wt % |
| Device 26 | Formula (1-55) | Bphen | 5:4 | Rubrene | 5 wt % |
| Device 27 | Formula (1-60) | TPBi | 6:3 | DCJTB | 5 wt % |
| Device 28 | Formula (1-65) | BAlq | 7:2 | DBQA | 15 wt % |
| Device 29 | Formula (1-78) | TmPyPB | 8:1 | DCM2 | 5 wt % |
| Device 30 | Formula (1-86) | Bphen | 9:1 | Rubrene | 5 wt % |

Embodiments 31-45

Devices 31-45 of these embodiments have the following structure:

glass/ITO/TADF:hole transport type material:phosphorescence material/cathode

Wherein, the respective materials and mass ratios of the TADF, the hole transport type material and the phosphorescence material are listed in Table 4.

Wherein the doping concentration of the phosphorescence material refers to the ratio that the phosphorescence material accounts for in the total mass of the light emitting layer, that is, the phosphorescence material doping concentration=the phosphorescence material mass/(the phosphorescence material mass+the TADF mass+the hole transport type material mass)*100%.

The preparation method of the devices 31-45 comprises the step of evaporation coating an anode layer (ITO), a light emitting layer and a cathode layer (cathode) in sequence on a substrate by using an open mask, wherein the light emitting layer is prepared by co-evaporation coating of a host material (TADF:hole transport type material) and a phosphorescence material.

TABLE 4

|  | TADF | Hole transport type material | Mass ratio | phosphorescence material | doping concentration of the phosphorescence material |
|---|---|---|---|---|---|
| Device 31 | Formula (1-32) | NPB | 1:9 | Ir(ppy)$_3$ | 30 wt % |
| Device 32 | Formula (1-33) | TCTA | 2:8 | Ir(ppy)$_2$(acac) | 15 wt % |
| Device 33 | Formula (1-34) | CBP | 3:7 | FIrPic | 5 wt % |
| Device 34 | Formula (1-56) | mCP | 4:5 | Ir(2-phq)$_2$(acac) | 15 wt % |
| Device 35 | Formula (1-36) | TPD | 5:4 | Ir(ppy)$_2$(acac) | 30 wt % |
| Device 36 | Formula (1-37) | TAPC | 6:3 | Ir(btpy)$_3$ | 20 wt % |
| Device 37 | Formula (1-38) | CBP | 7:2 | Be(pp)$_2$ | 5 wt % |
| Device 38 | Formula (1-39) | mCP | 8:1 | Ir(piq)$_2$(acac) | 15 wt % |
| Device 39 | Formula (1-41) | mCP | 9:1 | Ir(ppy)$_3$ | 30 wt % |
| Device 40 | Formula (1-42) | NPB | 1:9 | FIrPic | 5 wt % |
| Device 41 | Formula (1-43) | CBP | 2:8 | Ir(piq)$_2$(acac) | 15 wt % |
| Device 42 | Formula (1-44) | TAPC | 3:7 | Ir(ppy)$_2$(acac) | 15 wt % |
| Device 43 | Formula (1-46) | NPB | 4:5 | FIr6 | 10 wt % |
| Device 44 | Formula (1-47) | TCTA | 5:4 | Ir(piq)$_2$(acac) | 30 wt % |
| Device 45 | Formula (1-49) | CBP | 6:3 | Be(pp)$_2$ | 5 wt % |

Embodiments 46-60

Devices 46-60 of these embodiments have the following structure:

glass/ITO/TADF:electron transport type material:phosphorescence material/cathode Wherein, the respective materials and mass ratios of the TADF, the electron transport type material and the phosphorescence material are listed in Table 5.

Wherein the doping concentration of the phosphorescence material refers to the ratio that the phosphorescence material accounts for in the total mass of the light emitting layer, that is, the phosphorescence material doping concentration=the phosphorescence material mass/(the phosphorescence material mass+the TADF mass+the electron transport type material mass)*100%.

The preparation method of the devices 46-60 comprises the step of evaporation coating an anode layer (ITO), a light emitting layer and a cathode layer (cathode) in sequence on a substrate by using an open mask, wherein the light emitting layer is prepared by co-evaporation coating of a host material (TADF:electron transport type material) and a phosphorescence material.

TABLE 5

| | TADF | Electron transport type material | Mass ratio | phosphorescence material | doping concentration of the phosphorescence material |
|---|---|---|---|---|---|
| Device 46 | Formula (1-52) | BAlq | 1:9 | Ir(ppy)$_3$ | 30 wt % |
| Device 47 | Formula (1-53) | TPBi | 2:8 | Ir(ppy)$_2$(acac) | 15 wt % |
| Device 48 | Formula (1-54) | Bphen | 3:7 | FIrPic | 5 wt % |
| Device 49 | Formula (1-57) | Bphen | 4:5 | Ir(2-phq)$_2$(acac) | 15 wt % |
| Device 50 | Formula (1-58) | Alq3 | 5:4 | Ir(ppy)$_2$(acac) | 30 wt % |
| Device 51 | Formula (1-59) | Alq$_3$ | 6:3 | Ir(btpy)$_3$ | 20 wt % |
| Device 52 | Formula (1-72) | Bphen | 7:2 | Be(pp)$_2$ | 5 wt % |
| Device 53 | Formula (1-76) | BCP | 8:1 | Ir(piq)$_2$(acac) | 15 wt % |
| Device 54 | Formula (1-80) | TmPyPB | 9:1 | Ir(ppy)$_3$ | 30 wt % |
| Device 55 | Formula (1-82) | TPBi | 1:9 | FIrPic | 5 wt % |
| Device 56 | Formula (1-83) | BAlq | 2:8 | Ir(piq)$_2$(acac) | 15 wt % |
| Device 57 | Formula (1-85) | TPBi | 3:7 | Ir(ppy)$_2$(acac) | 15 wt % |
| Device 58 | Formula (1-63) | BCP | 4:5 | FIr6 | 10 wt % |
| Device 59 | Formula (1-68) | Bphen | 5:4 | Ir(piq)$_2$(acac) | 30 wt % |
| Device 60 | Formula (1-66) | BCP | 6:3 | Be(pp)$_2$ | 5 wt % |

Embodiments 61-74

Devices 61-74 of these embodiments have the following structure:

glass/ITO/TADF:dye/cathode

Wherein, the materials and mass ratios of the dye as in the (TADF:dye) are listed in Table 6.

Wherein the dye is a fluorescence material and/or a phosphorescence material, the doping concentration of the dye refers to the ratio that the dye accounts for in the total mass of the light emitting layer, that is, the dye doping concentration=the dye mass/(the dye mass+the TADF mass)*100%.

The preparation method of the devices 61-74 comprises the step of evaporation coating an anode layer (ITO), a light emitting layer and a cathode layer (cathode) in sequence on a substrate by using an open mask, wherein the light emitting layer is prepared by co-evaporation coating of a host material TADF and a dye.

TABLE 6

| | TADF | Dye | Dye name | dye doping concentration |
|---|---|---|---|---|
| Device 61 | Formula (1-87) | fluorescence | TMDBQA | 10 wt % |
| Device 62 | Formula (1-88) | fluorescence | DMQA | 5 wt % |
| Device 63 | Formula (1-89) | fluorescence | DPAVBi | 5 wt % |
| Device 64 | Formula (1-90) | fluorescence | BCzVBi | 5 wt % |
| Device 65 | Formula (1-91) | fluorescence | DCJT | 5 wt % |
| Device 66 | Formula (1-92) | fluorescence | DCJTB | 5 wt % |
| Device 67 | Formula (1-93) | fluorescence | Rubrene | 5 wt % |
| Device 68 | Formula (1-94) | phosphorescence | Ir(ppy)$_3$ | 30 wt % |
| Device 69 | Formula (1-95) | phosphorescence | Ir(ppy)$_2$(acac) | 15 wt % |
| Device 70 | Formula (1-96) | phosphorescence | FIrPic | 5 wt % |
| Device 71 | Formula (1-97) | phosphorescence | Ir(2-phq)$_2$(acac) | 15 wt % |
| Device 72 | Formula (1-98) | phosphorescence | Ir(ppy)$_2$ (acac) | 30 wt % |
| Device 73 | Formula (1-99) | phosphorescence | Ir(btpy)$_3$ | 20 wt % |
| Device 74 | Formula (1-100) | phosphorescence | Be(pp)$_2$ | 5 wt % |

Test results of performance of some devices of the above-mentioned Devices 4-74 are listed as follows:

| Device | Brightness (cd/m$^2$) | Luminous efficiency (cd/A) | External quantum efficiency (%) | Service life T$_{90}$ (hrs) |
|---|---|---|---|---|
| Device 4 | 5000 | 20 | 17 | 520 |
| Device 8 | 5000 | 17 | 16 | 498 |
| Device 10 | 1000 | 10 | 4 | 163 |
| Device 12 | 1000 | 9 | 3 | 150 |
| Device 15 | 1000 | 6 | 5 | 155 |
| Device 18 | 1000 | 8 | 5 | 164 |
| Device 20 | 1000 | 8 | 5 | 160 |
| Device 24 | 5000 | 20 | 19 | 392 |
| Device 26 | 5000 | 16 | 17 | 511 |
| Device 30 | 5000 | 17 | 17 | 509 |
| Device 35 | 5000 | 60 | 16 | 398 |
| Device 40 | 1000 | 4 | 6 | 89 |
| Device 48 | 1000 | 4 | 5 | 79 |
| Device 55 | 1000 | 6 | 5 | 80 |
| Device 62 | 5000 | 19 | 17 | 355 |
| Device 68 | 5000 | 57 | 15 | 472 |
| Device 70 | 1000 | 5 | 6 | 74 |
| Device 72 | 5000 | 52 | 14 | 394 |
| Device 74 | 1000 | 7 | 13 | 88 |

Embodiments of synthesis of the compound of formula (1-85) to (1-98):

Embodiment 75

The synthesis method of the compound of formula (1-85) is as follows: in a nitrogen atmosphere, 1 mol potassium tert-butoxide is dissolved in 20 mL DML with stirring for 1 hour, then a DML solution containing 1 mol carbazole is added dropwise therein, after that the resultant solution is stirred for 1 hour; then, a DMF solution containing 0.2 mol 2,3,4,5,6-pentafluorobenzonitrile is added dropwise therein, after that the resultant solution is stirred for 5 hours; then, the reacted liquid is poured into water, and solid is obtained after filtration and separated by using a chromatographic column. Thereby the compound of formula (1-85) is produced, with a yield rate of 90%.

Mass spectrum: 929.

Element analysis: C: 86.60, H: 4.35, N: 9.05.

Embodiment 76

In the synthesis method of the compound of formula (1-86), the reactant carbazole is replaced by tert-butyl carbazole, and a synthesis process similar to that of Embodiment 75 is carried out to produce the compound of formula (1-86), with a yield rate of 91%.
Mass spectrum: 1490.
Element analysis: C: 86.20, H: 8.16, N: 5.64.

Embodiment 77

In the synthesis method of the compound of formula (1-87), the reactant carbazole is replaced by phenyl carbazole, and a synthesis process similar to that of Embodiment 75 is carried out to produce the compound of formula (1-87), with a yield rate of 91%.
Mass spectrum: 1689.
Element analysis: C: 90.20, H: 4.83, N: 4.97.

Embodiment 78

The synthesis method of the compound of formula (1-88) is as follows: in a nitrogen atmosphere, 1 mol potassium tert-butoxide is dissolved in 20 mL DML with stirring for 1 hour, then a DML solution containing 1 mol carbazole is added dropwise therein, after that the resultant solution is stirred for 1 hour; then, a DMF solution containing 0.25 mol 2,3,5,6-tetrafluorobenzonitrile is added dropwise therein, after that the resultant solution is stirred for 5 hours; then, the reacted liquid is poured into water, and solid is obtained after filtration and separated by using a chromatographic column. Thereby the compound of formula (1-88) is produced, with a yield rate of 90%.
Mass spectrum: 763.
Element analysis: C: 86.47, H: 4.36, N: 9.17.

Embodiment 79

In the synthesis method of the compound of formula (1-89), the reactant carbazole is replaced by tert-butyl carbazole, and a synthesis process similar to that of Embodiment 78 is carried out to produce the compound of formula (1-89), with a yield rate of 91%.
Mass spectrum: 1212.
Element analysis: C: 86.15, H: 8.07, N: 5.77.

Embodiment 80

In the synthesis method of the compound of formula (1-90), the reactant carbazole is replaced by methyl carbazole, and a synthesis process similar to that of Embodiment 78 is carried out to produce the compound of formula (1-90), with a yield rate of 91%.
Mass spectrum: 876.
Element analysis: C: 86.36, H: 5.65, N: 7.99.

Embodiment 81

In the synthesis method of the compound of formula (1-91), the reactant carbazole is replaced by phenyl carbazole, and a synthesis process similar to that of Embodiment 78 is carried out to produce the compound of formula (1-91), with a yield rate of 91%.
Mass spectrum: 1372.
Element analysis: C: 90.10, H: 4.79, N: 5.10.

Embodiment 82

In the synthesis method of the compound of formula (1-92), the reactant carbazole is replaced by methoxyl carbazole, and a synthesis process similar to that of Embodiment 78 is carried out to produce the compound of formula (1-92), with a yield rate of 91%.
Mass spectrum: 1004.
Element analysis: C: 75.35, H: 4.93, N: 6.97.

Embodiment 83

The synthesis method of the compound of formula (1-93) is as follows: in a nitrogen atmosphere, 1 mol potassium tert-butoxide is dissolved in 20 mL DML with stirring for 1 hour, then a DML solution containing 1 mol methoxyl carbazole is added dropwise therein, after that the resultant solution is stirred for 1 hour; then, a DMF solution containing 0.33 mol 2,4,6-trifluorobenzonitrile is added dropwise therein, after that the resultant solution is stirred for 5 hours; then, the reacted liquid is poured into water, and solid is obtained after filtration and separated by using a chromatographic column. Thereby the compound of formula (1-93) is produced, with a yield rate of 90%.
Mass spectrum: 778.
Element analysis: C: 75.55, H: 4.93, N: 7.19.

Embodiment 84

In the synthesis method of the compound of formula (1-94), the reactant carbazole is replaced by tert-butyl carbazole, and a synthesis process similar to that of Embodiment 83 is carried out to produce the compound of formula (1-94), with a yield rate of 91%.
Mass spectrum: 935.
Element analysis: C: 86.00, H: 7.81, N: 5.99.

Embodiment 85

In the synthesis method of the compound of formula (1-95), the reactant carbazole is replaced by phenoxazine, and a synthesis process similar to that of Embodiment 83 is carried out to produce the compound of formula (1-95), with a yield rate of 91%.
Mass spectrum: 829.
Element analysis: C: 79.79, H: 4.00, N: 8.48.

Embodiment 86

In the synthesis method of the compound of formula (1-96), the reactant carbazole is replaced by phenothiazine, and a synthesis process similar to that of Embodiment 83 is carried out to produce the compound of formula (1-96), with a yield rate of 91%.
Mass spectrum: 892.
Element analysis: C: 74.05, H: 3.70, N: 7.88.

Embodiment 87

In the synthesis method of the compound of formula (1-97), the reactant carbazole is replaced by acridine, and a synthesis process similar to that of Embodiment 83 is carried out to produce the compound of formula (1-97), with a yield rate of 91%.
Mass spectrum: 932.
Element analysis: C: 86.32, H: 6.15, N: 7.52.

Embodiment 88

In the synthesis method of the compound of formula (1-98), the reactant carbazole is replaced by phenazine, and a synthesis process similar to that of Embodiment 83 is carried out to produce the compound of formula (1-98), with a yield rate of 91%.

Mass spectrum: 880.

Element analysis: C: 80.50, H: 5.17, N: 14.32.

Apparently, the aforementioned embodiments are merely examples illustrated for clearly describing the present invention, rather than limiting the implementation ways thereof. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present invention.

The invention claimed is:

1. An organic electroluminescent device, comprising a substrate and light emitting units formed in sequence on the substrate, wherein each of the light emitting units consists of a first electrode layer (1), a light emitting layer (2) and a second electrode layer (3), the light emitting layer comprises a host material and a dye, the host material is an exciplex made from at least two different kinds of thermal activating delayed fluorescence material, or an exciplex made from at least one kind of thermal activating delayed fluorescence material and a hole transport type material, or an exciplex made from at least one kind of thermal activating delayed fluorescence material and an electron transport type material;

wherein the exciplex serving as the host material has a CT excited triplet state energy level $T_1$ greater than its n-π excited triplet state energy level $S_1$, and $T_1-S_1 \leq 0.3$ eV; or wherein the exciplex serving as the host material has a CT excited triplet state energy level $T_1$ greater than its n-π excited triplet state energy level $S_1$, and $T_1-S_1 \geq 1$ eV, with the difference between its n-π excited second triplet state energy level and its CT excited first singlet state energy being in the range of −0.1 eV to 0.1 eV, and the thermal activating delayed fluorescence material has a structure selected from the following structural formulas (1-2), (1-6) to (1-10), (1-12) to (1-15), (1-19) to (1-21), (1-24), (1-25), (1-27) to (1-48), (1-55), (1-59), (1-61), (1-69) to (1-100):

1-2

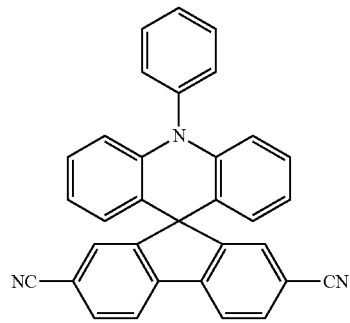

1-6

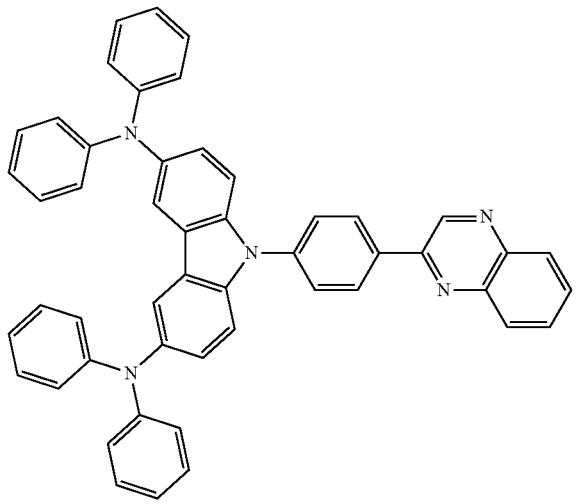

1-7

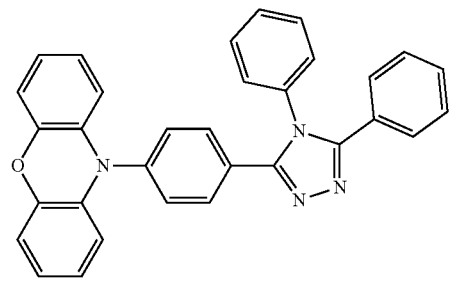

1-8

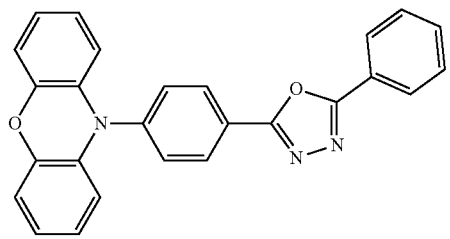

-continued
1-9
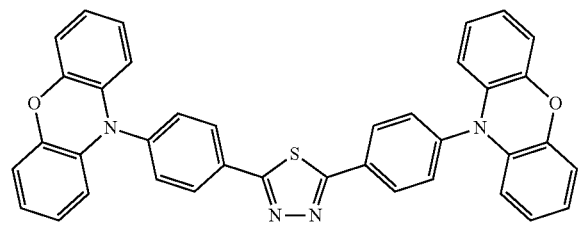
1-10
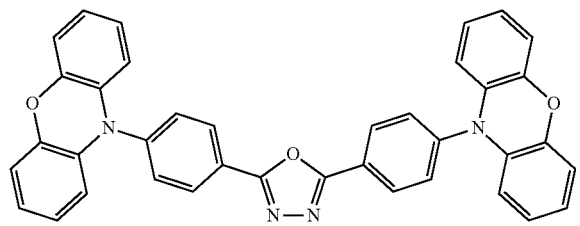
1-12
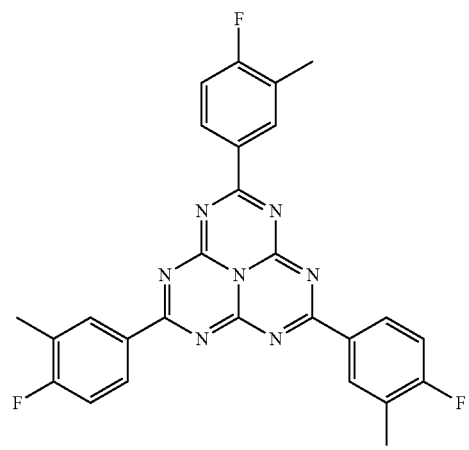
1-13
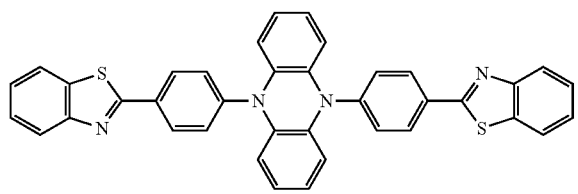
1-14
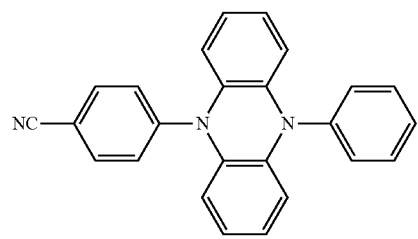
1-15
1-19
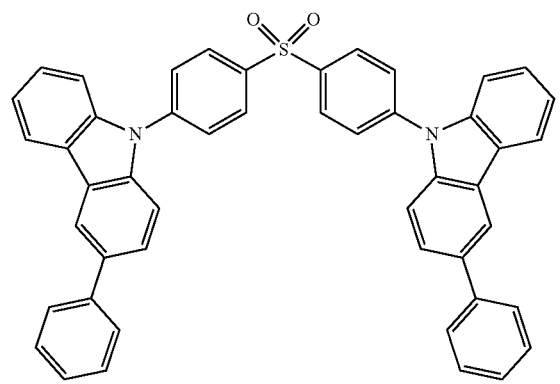
1-20
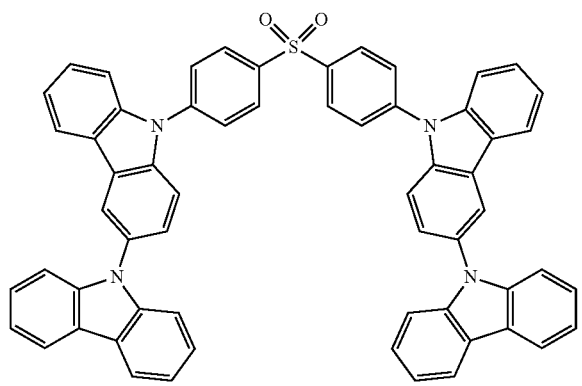

-continued
1-21
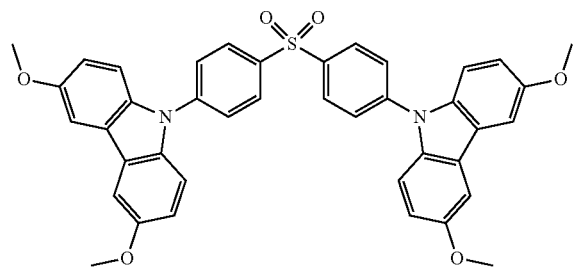
1-24
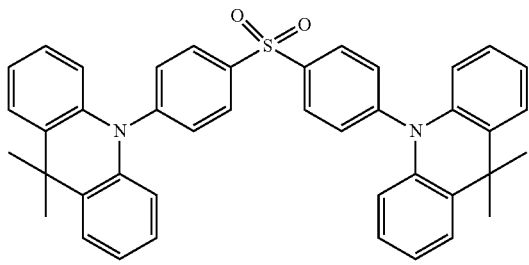
1-25
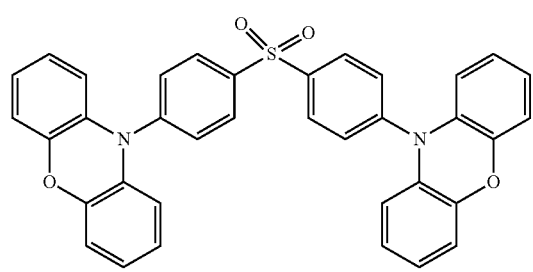
1-27
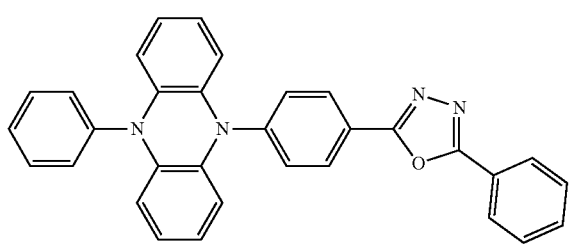
1-28
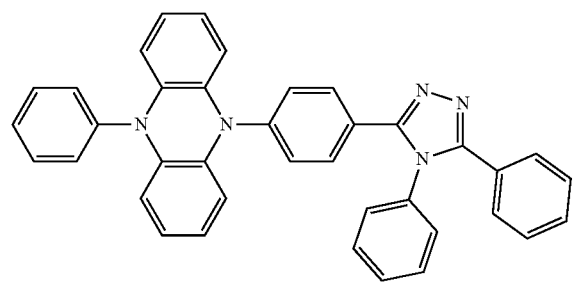
1-29
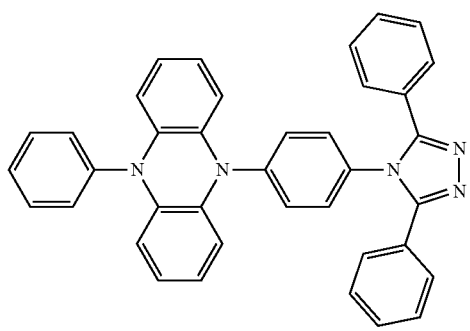
1-30
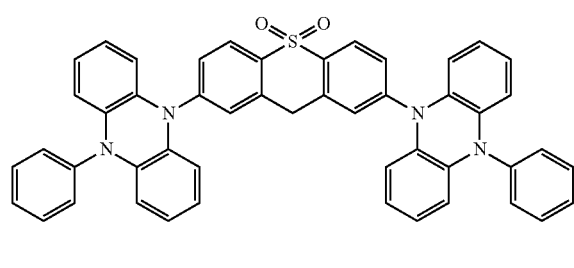
1-31
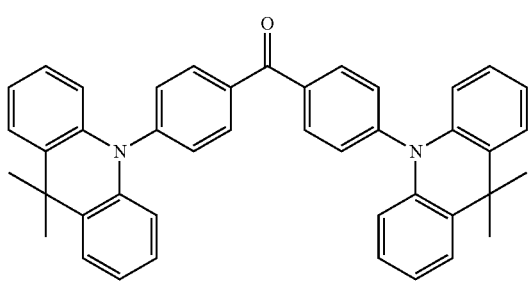
1-32
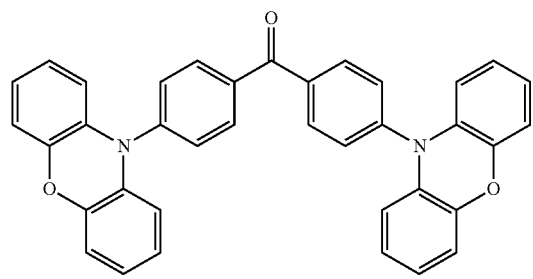
1-33
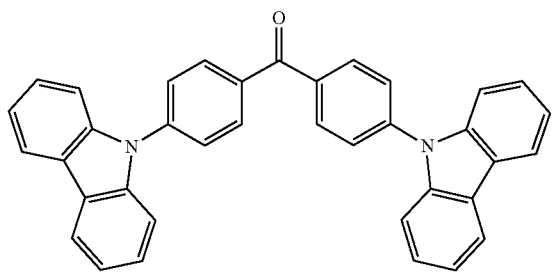

1-34
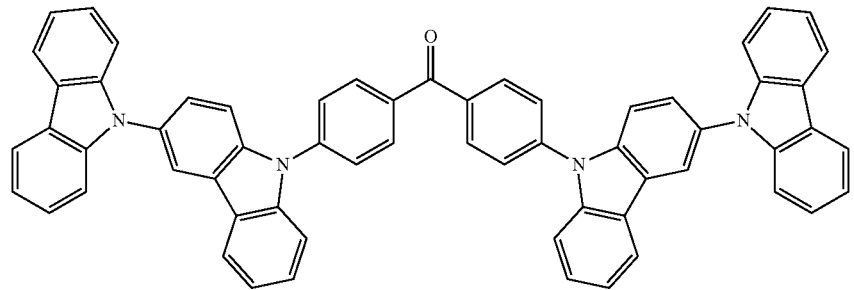
1-35
1-36
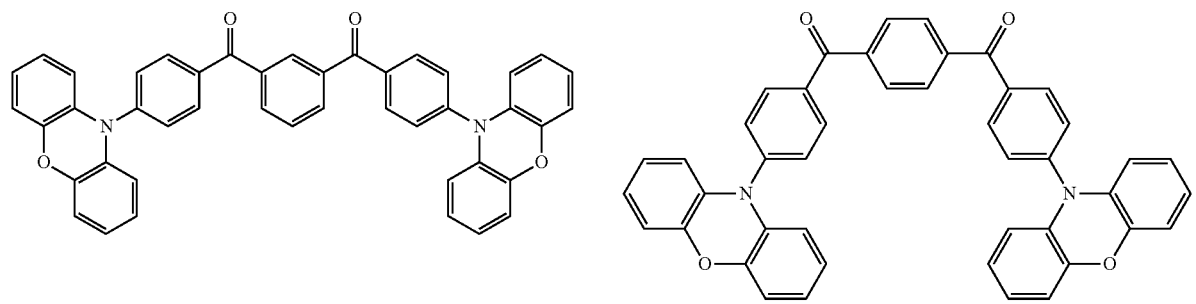
1-37
1-38
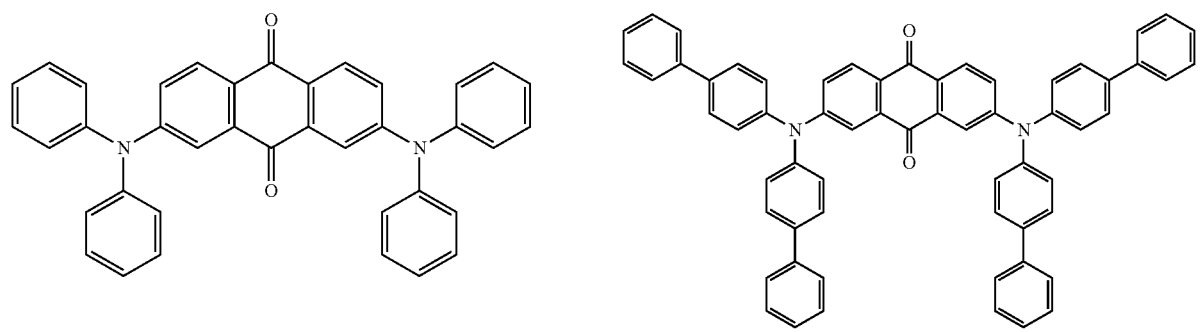
1-39
1-40
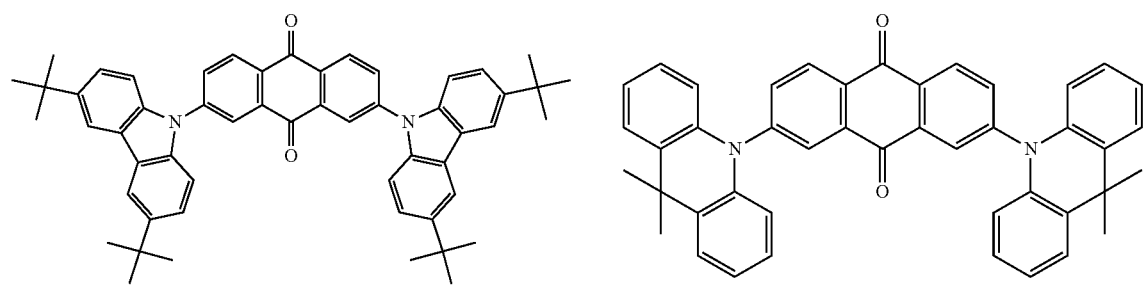

1-41
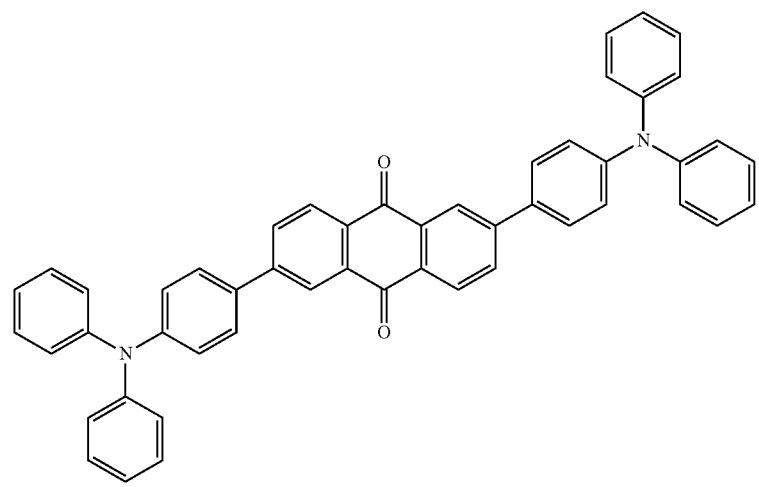
1-42
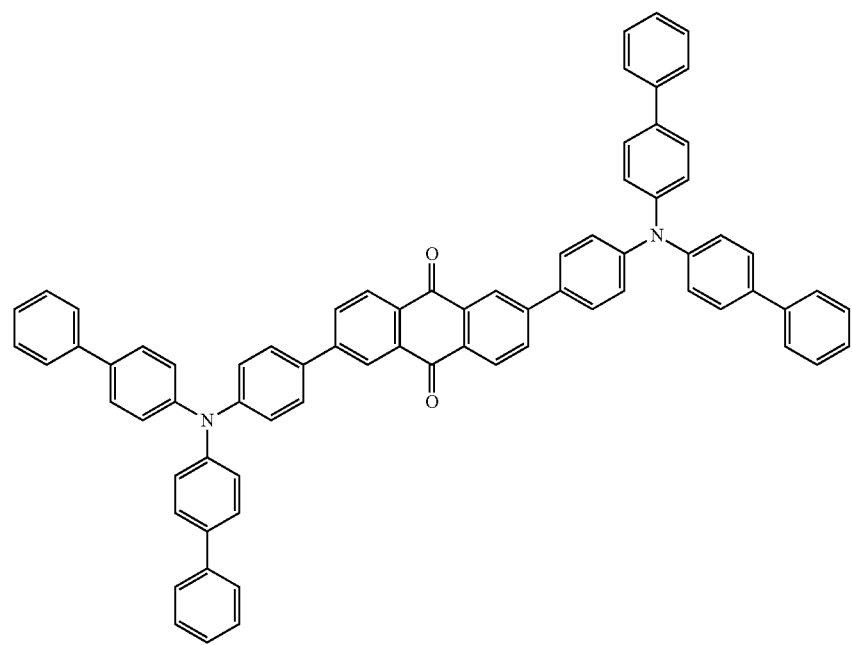

-continued
1-43
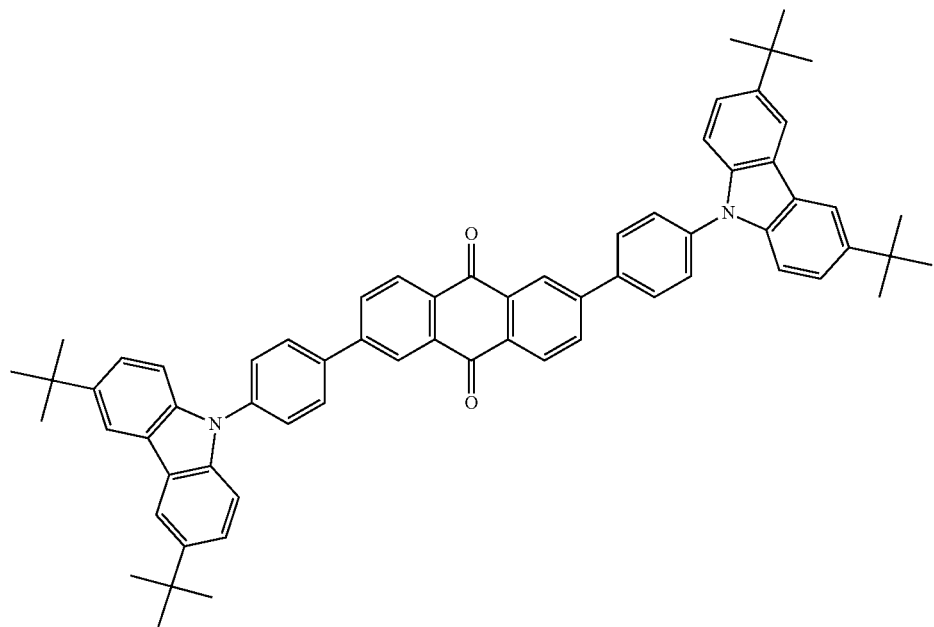
1-44
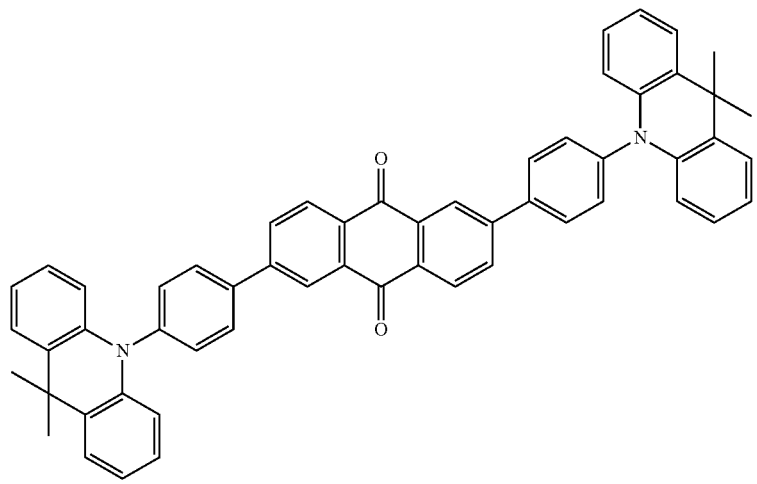
1-45
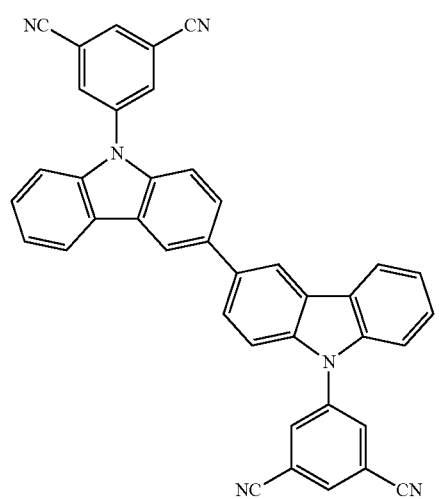
1-46
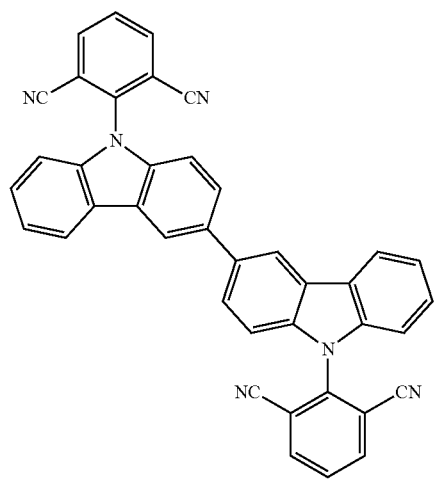

-continued
1-47
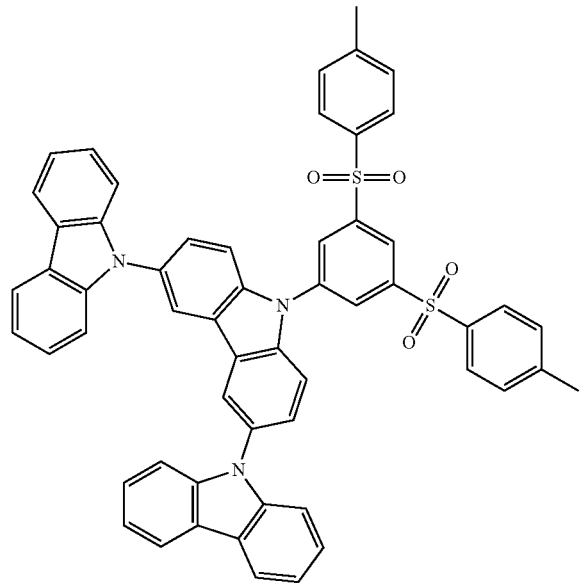
1-48
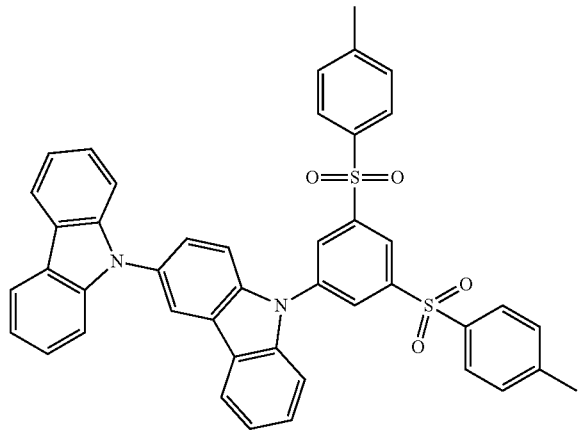
1-55
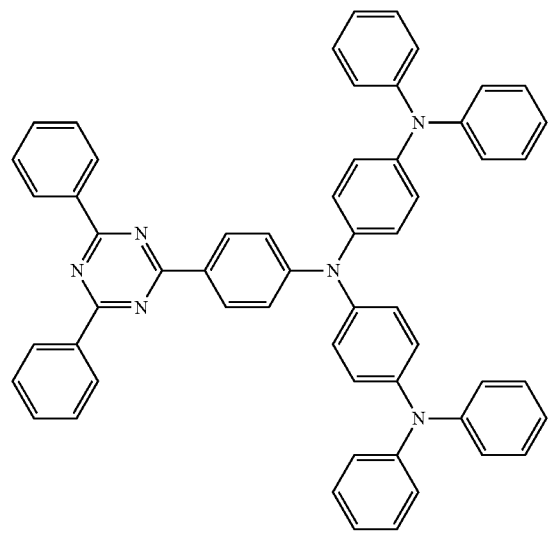
1-59
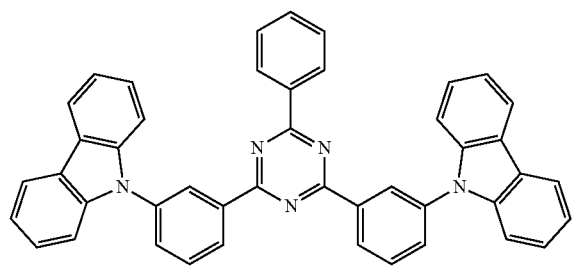
1-61
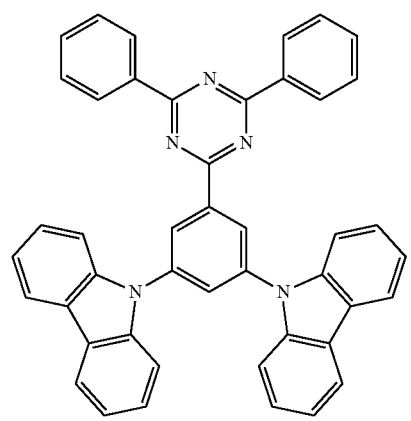
1-69
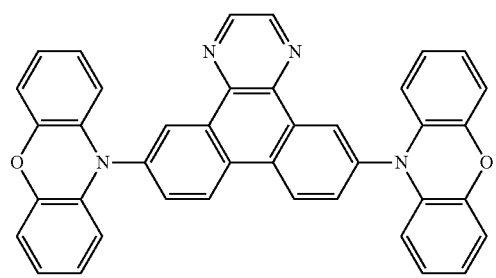

-continued
1-70
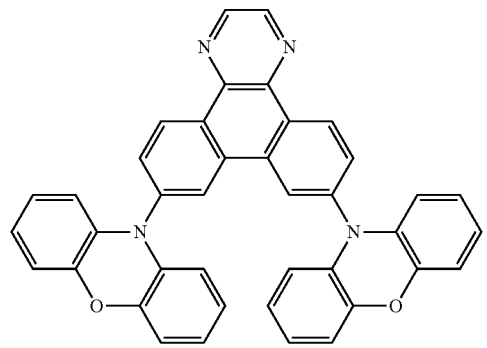
1-71
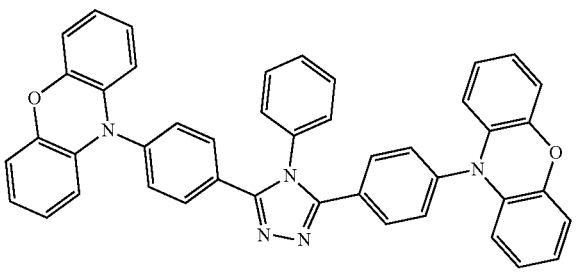
1-72
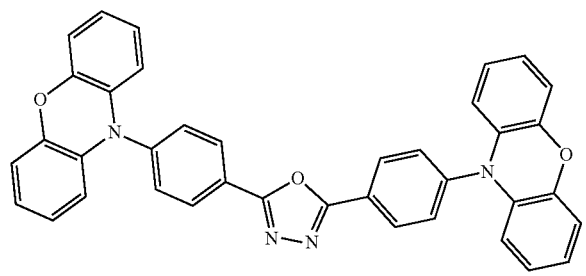
1-73
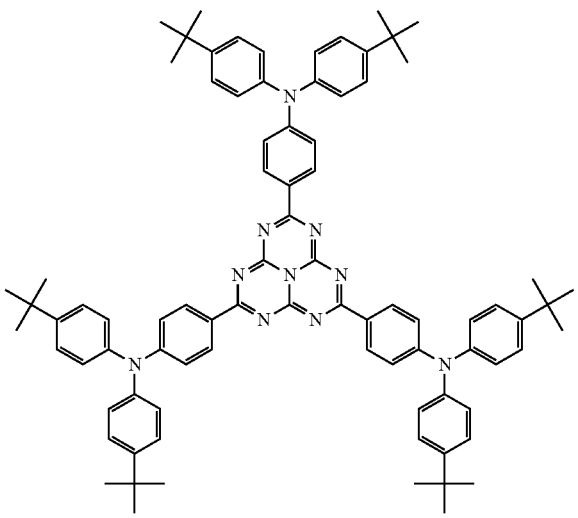
1-74
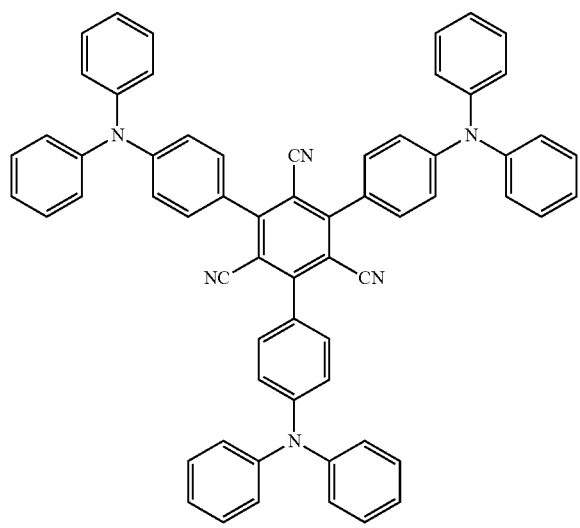
1-75
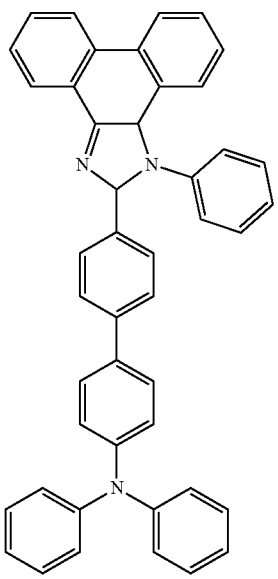

-continued
1-76 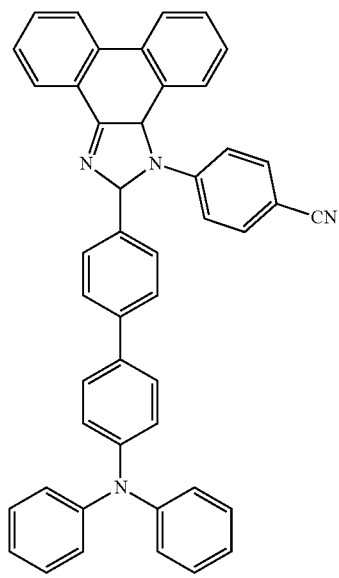
1-77 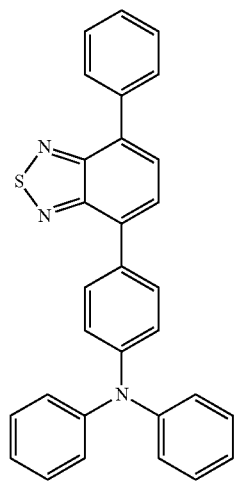
1-78 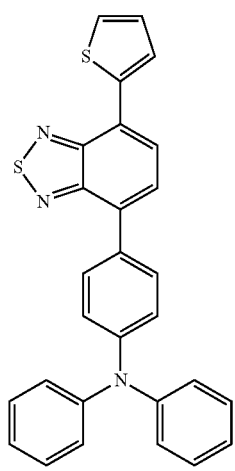
1-79 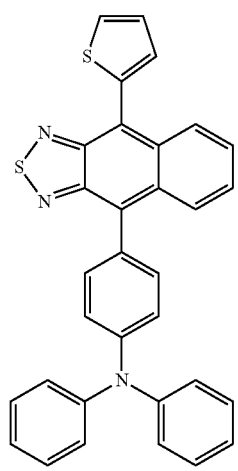
1-80 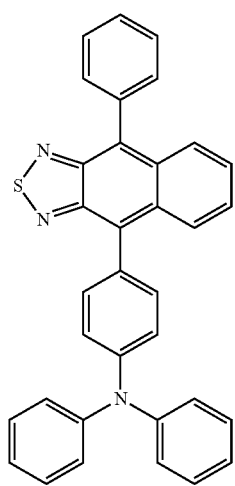
1-81 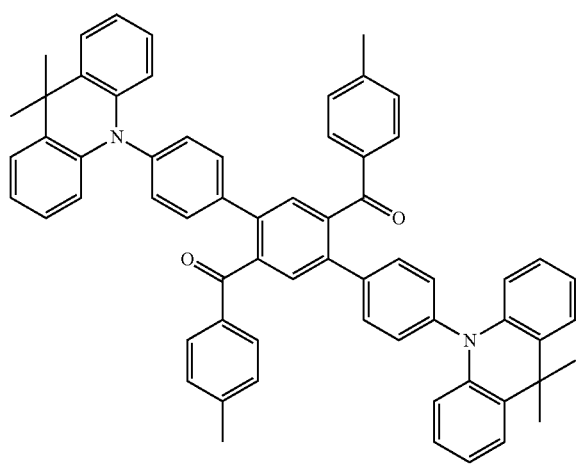

-continued
| 1-82 | 1-83 |
|---|---|
| 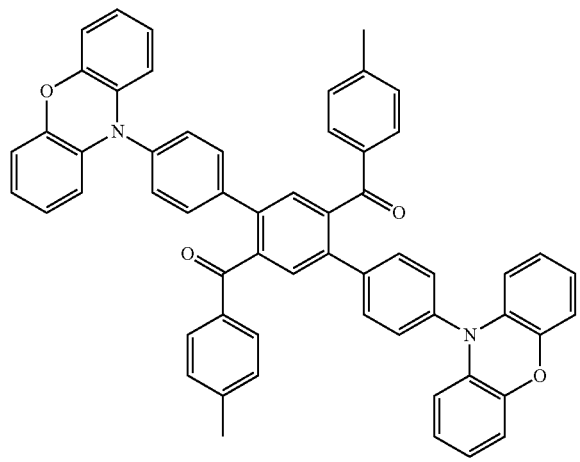 | 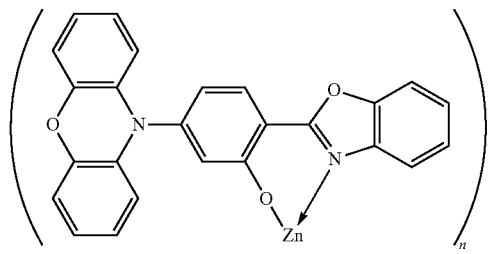 |
| 1-84 | 1-85 |
| 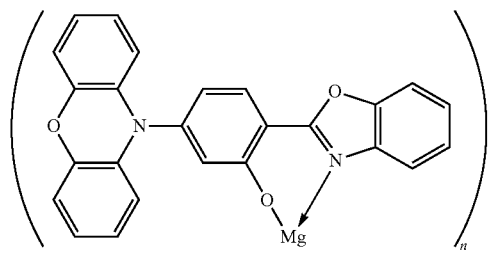 | 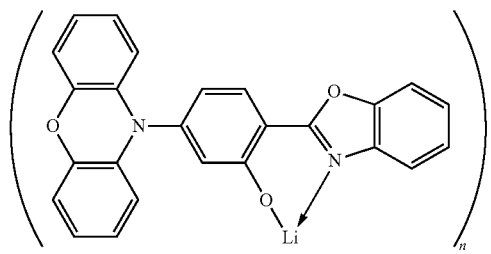 |
| 1-86 | 1-87 |
| 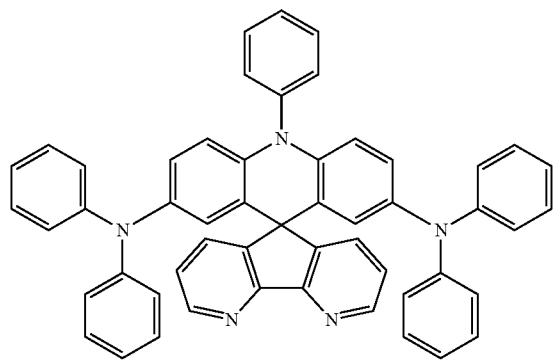 | 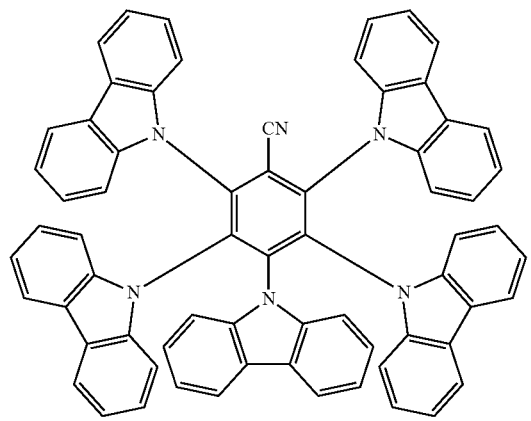 |

-continued
1-88
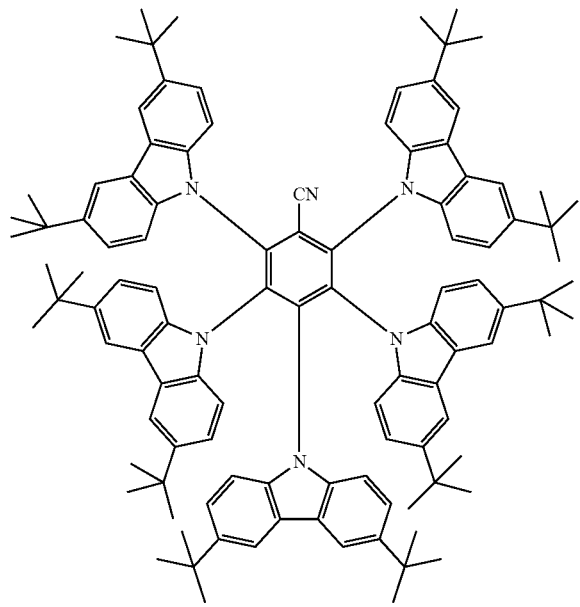
1-89
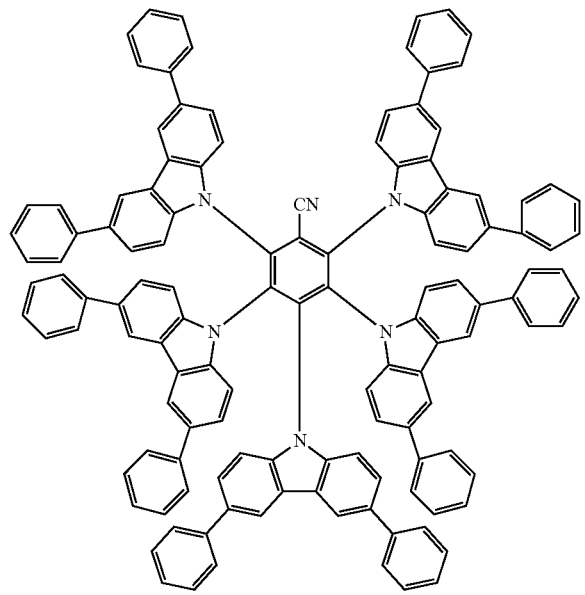
1-90
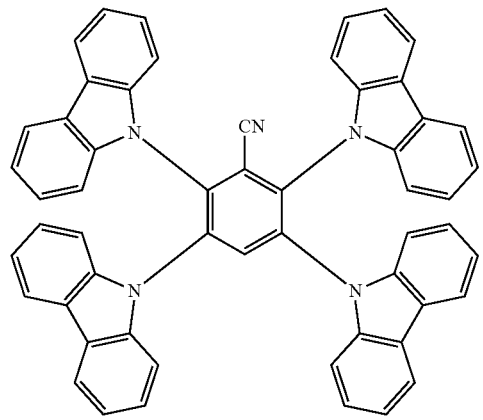
1-91
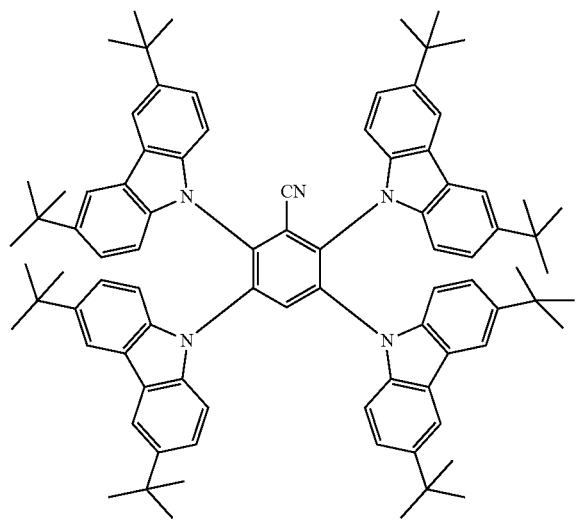

-continued
1-92
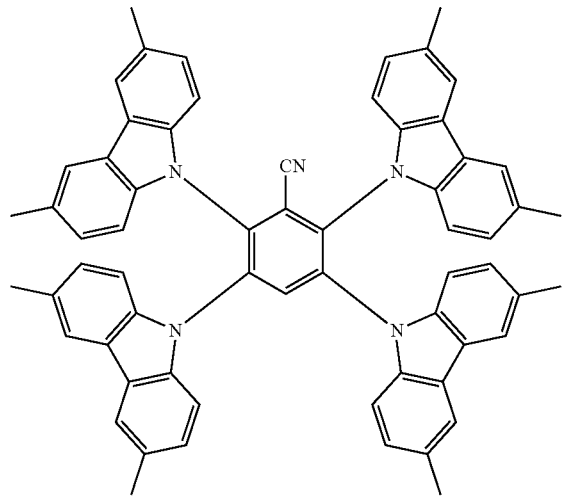
1-93
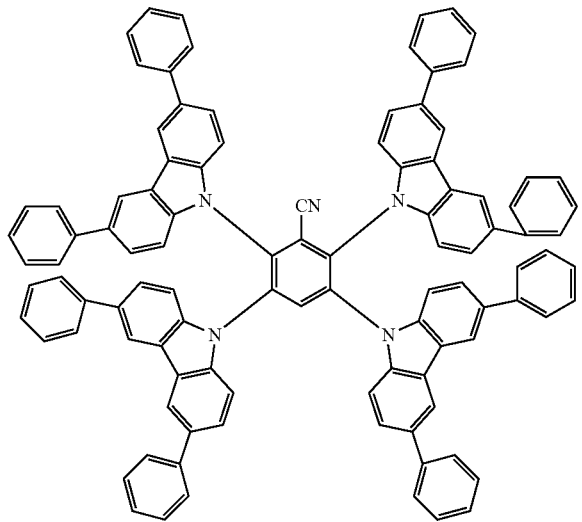
1-94
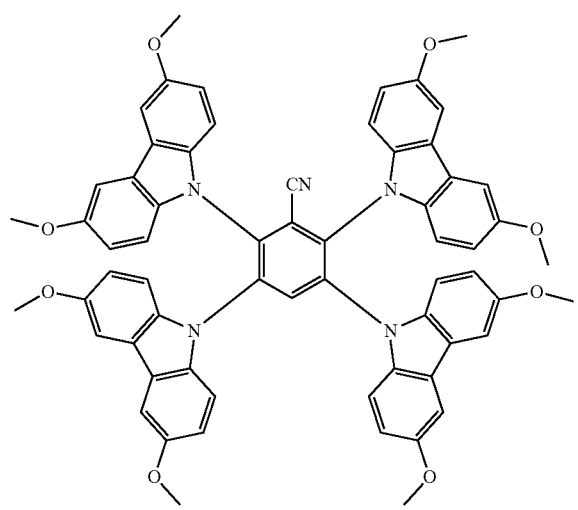
1-95
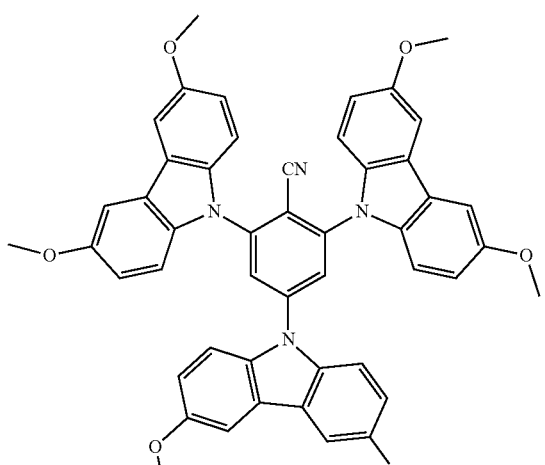
1-96
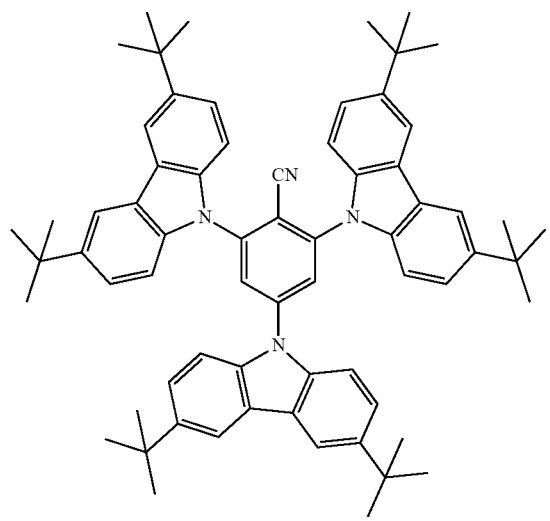
1-97
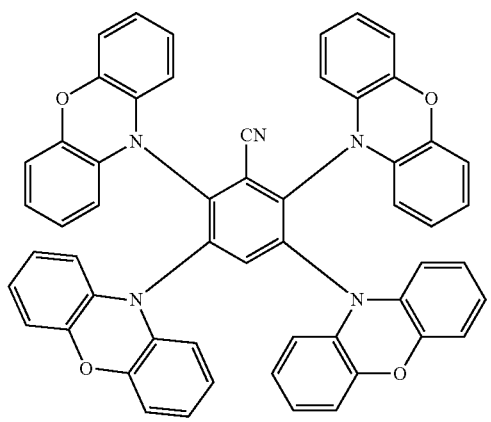

-continued

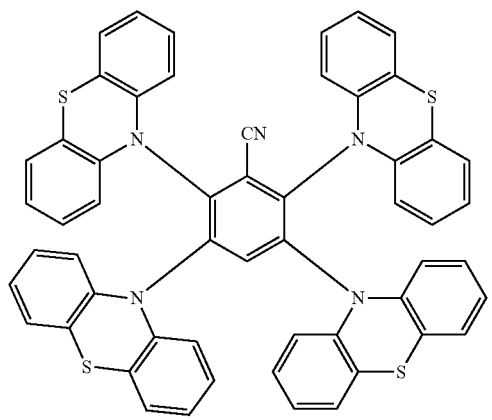
1-98

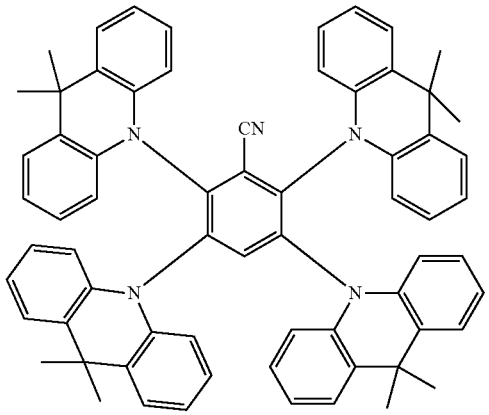
1-99

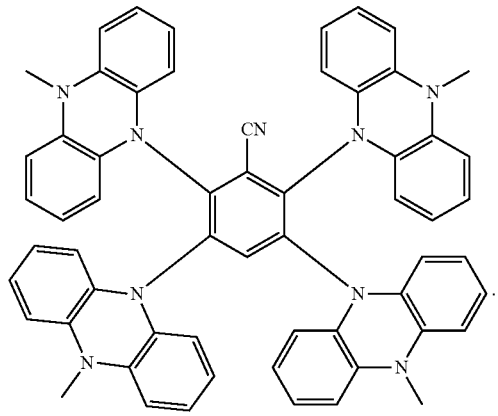
1-100

2. The organic electroluminescent device in accordance with claim 1, wherein the host material is an exciplex made from a thermal activating delayed fluorescence material selected from the structural formulas (1-2), (1-6) to (1-10), (1-12) to (1-15), (1-19) to (1-21), (1-24), (1-25), (1-27) to (1-48), (1-55), (1-59), (1-61), (1-69) to (1-100) and a hole transport type material at a mass ratio of 1:9 to 9:1, the hole transport type material is N,N'-di-(1-naphthyl)-N,N'-diphenyl-1,1'-biphenyl-4,4'-diamine, N,N'-diphenyl-N,N'-di-(m-methyl-phenyl)-1,1'-biphenyl-4,4'-diamine, 4,4'-cyclohexyl-di-[N,N-di-(4-methyl-phenyl)]-phenylamine, 4,4'-N,N'-di-carbazole-biphenyl, 4,4',4"-tri-(carbazole-9-yl)-triphenylamine, or 1,3-di-(carbazole-9-yl)-benzene.

3. The organic electroluminescent device in accordance with claim 1, wherein the host material is an exciplex made from a thermal activating delayed fluorescence material selected from the structural formulas (1-2), (1-6) to (1-10), (1-12) to (1-15), (1-19) to (1-21), (1-24), (1-25), (1-27) to (1-48), (1-55), (1-59), (1-61), (1-69) to (1-100) and an electron transport type material at a mass ratio of 1:9 to 9:1, the electron transport type material is tri-(8-oxyquinoline)-aluminum, 2,9-dimethyl-4,7-diphenyl-1,10-o-phenanthroline, 4,7-diphenyl-1,10-o-phenanthroline, di-(2-methyl-8-quinolyl)-4-phenyl-phenoxide-aluminum(III), 1,3,5-tri-(1-phenyl-1H-benzimidazole-2-yl)-benzene, or 1,3,5-tri-[(3-pyridyl)-3-phenyl]-benzene.

4. The organic electroluminescent device in accordance with claim 1, wherein the dye is made of a fluorescence material and/or a phosphorescence material, the fluorescence material has a doping concentration of 0.5-10 wt %, the phosphorescence material has a doping concentration of 0.5-20 wt %.

5. The organic electroluminescent device in accordance with claim 1, wherein the light emitting layer (2) has a thickness of 50 nm-150 nm.

6. The organic electroluminescent device in accordance with claim 1, wherein, the host material is an exciplex made from at least two different kinds of thermal activating delayed fluorescence material selected from the structural formulas (1-2), (1-6) to (1-10), (1-12) to (1-15), (1-19) to (1-21), (1-24), (1-25), (1-27) to (1-48), (1-55), (1-59), (1-61), (1-69) to (1-100).

7. A preparation method of the organic electroluminescent device of claim 1, comprising the following steps:

evaporation coating a first electrode layer (1), a light emitting layer (2) and a second electrode layer (3) in sequence on a substrate by using an open mask;

wherein the light emitting layer (2) is prepared by co-evaporation coating of a host material and a dye.

* * * * *